United States Patent
Faries, Jr. et al.

[19]

[11] Patent Number: 5,879,621

[45] Date of Patent: *Mar. 9, 1999

[54] METHOD AND APPARATUS FOR ENSURING STERILITY OF SURGICAL DRAPES USED WITH SURGICAL EQUIPMENT

[75] Inventors: Durward I. Faries, Jr., McLean; Bruce R. Heymann, Vienna, both of Va.

[73] Assignee: O.R. Solutions, Inc., Chantilly, Va.

[*] Notice: The term of this patent shall not extend beyond the expiration date of Pat. No. 5,653,938.

[21] Appl. No.: 905,345

[22] Filed: Aug. 4, 1997

Related U.S. Application Data

[63] Continuation-in-part of Ser. No. 427,938, Apr. 26, 1995, Pat. No. 5,653,938.

[51] Int. Cl.⁶ .................... G05B 19/048; B01J 19/00
[52] U.S. Cl. .................... 422/3; 422/40; 422/105; 422/117; 422/119
[58] Field of Search .................... 422/3, 105, 117, 422/119, 40; 364/413.01, 507

[56] References Cited

U.S. PATENT DOCUMENTS

| | | | |
|---|---|---|---|
| 3,902,484 | 9/1975 | Winters | 128/132 D |
| 4,393,659 | 7/1983 | Keyes et al. | 62/66 |
| 4,474,016 | 10/1984 | Winchell | 62/60 |
| 4,522,041 | 6/1985 | Menzel | 62/342 |
| 4,782,835 | 11/1988 | Bernardini | 128/403 |
| 4,934,152 | 6/1990 | Templeton | 62/66 |
| 4,967,061 | 10/1990 | Webe, Jr. et al. | 219/438 |
| 5,040,699 | 8/1991 | Gangemi | 222/1 |
| 5,042,455 | 8/1991 | Yue et al. | 126/263 |
| 5,129,033 | 7/1992 | Ferrara et al. | 392/447 |
| 5,163,299 | 11/1992 | Faries, Jr. et al. | 62/66 |
| 5,174,306 | 12/1992 | Marshall | 128/849 |
| 5,310,524 | 5/1994 | Campbell et al. | 422/33 |
| 5,331,820 | 7/1994 | Faries, Jr. et al. | 62/68 |
| 5,333,326 | 8/1994 | Faries, Jr. et al. | 4/639 |
| 5,363,746 | 11/1994 | Gordon | 99/328 |
| 5,374,813 | 12/1994 | Shipp | 235/375 |
| 5,383,476 | 1/1995 | Peimer et al. | 128/849 |
| 5,386,835 | 2/1995 | Elphick et al. | 128/846 |
| 5,400,267 | 3/1995 | Denen et al. | 364/552 |
| 5,400,616 | 3/1995 | Faries, Jr. et al. | 62/340 |
| 5,402,644 | 4/1995 | Faries, Jr. et al. | 62/3.6 |
| 5,429,801 | 7/1995 | Faries, Jr. et al. | 422/41 |
| 5,435,322 | 7/1995 | Marshall | 128/849 |
| 5,443,082 | 8/1995 | Mewburn | 128/897 |
| 5,449,892 | 9/1995 | Yamada | 235/462 |
| 5,457,962 | 10/1995 | Faries, Jr. et al. | 62/68 |
| 5,463,213 | 10/1995 | Honda | 235/468 |
| 5,502,980 | 4/1996 | Faries, Jr. et al. | 62/342 |
| 5,522,095 | 6/1996 | Faries, Jr. et al. | 4/639 |
| 5,524,643 | 6/1996 | Faries, Jr. et al. | 128/849 |
| 5,551,240 | 9/1996 | Faries, Jr. et al. | 62/3.6 |
| 5,615,423 | 4/1997 | Faries, Jr. et al. | 4/639 |
| 5,653,938 | 8/1997 | Faries, Jr. et al. | 422/3 |

*Primary Examiner*—Krisanne Thornton

[57] ABSTRACT

The presence of a drape on a thermal treatment system for ensuring sterility of a sterile medium contained within a thermal treatment system basin is determined by the use of a drape identifier and corresponding detector. When a drape containing the identifier is placed on the corresponding thermal treatment system, a detector senses and verifies the drape identifier to determine the presence of the drape on the thermal treatment system. A controller receives a signal from the detector indicating whether or not a drape is present on the thermal treatment system. If a drape is not present on the thermal treatment system, the controller prevents thermal treatment system operation. Various drape identifiers may be utilized to indicate the presence of the drape on the thermal treatment system, such as bar codes, mechanical and optical keys, light filter patches disposed on the drape passing various intensities or bands of light, reflective material segments disposed on the drape or reflective material used to construct the drape itself for reflecting light from a light source toward a light detector, and magnetic media in the form of magnetic strips disposed on the drape or a magnetic pigment or resin additive incorporated into the drape material.

40 Claims, 9 Drawing Sheets

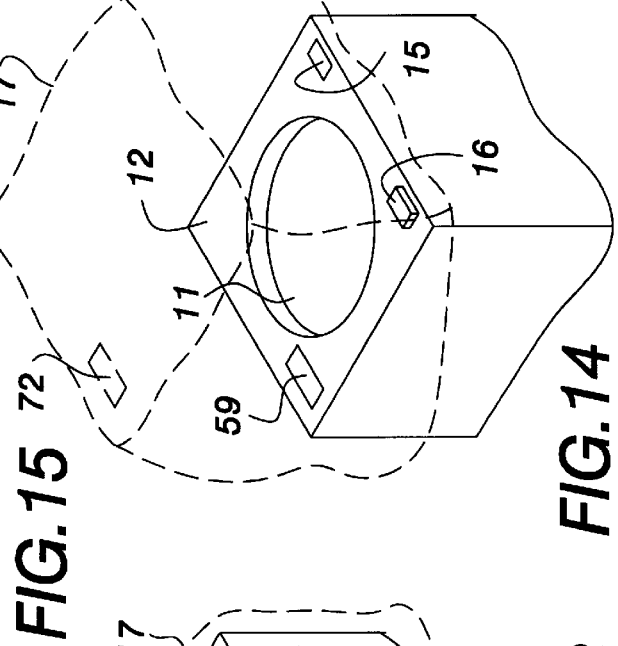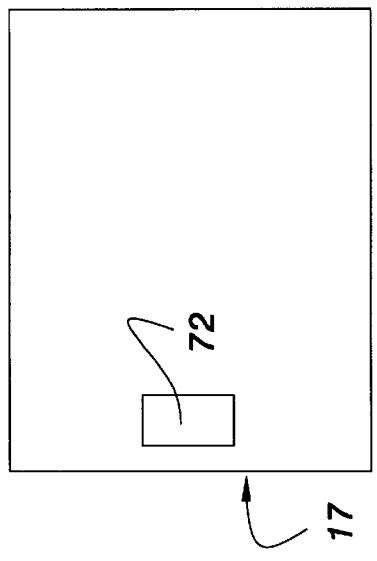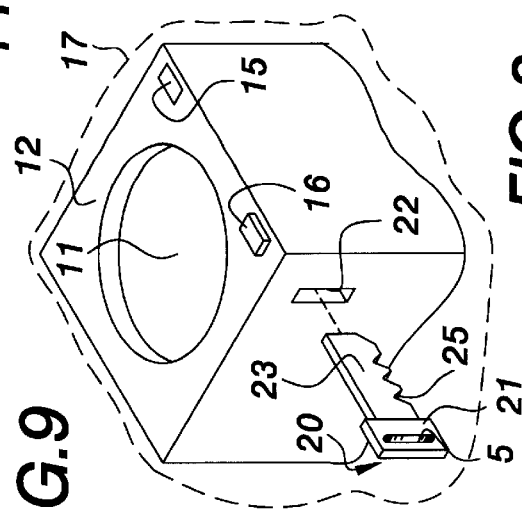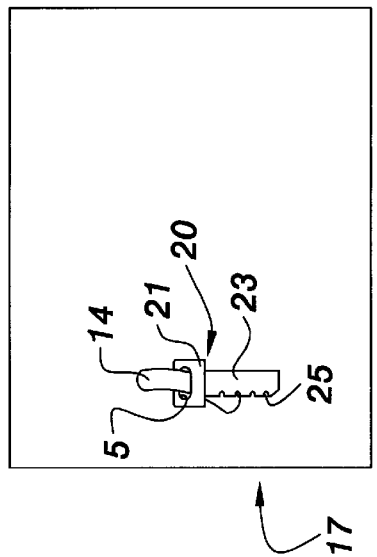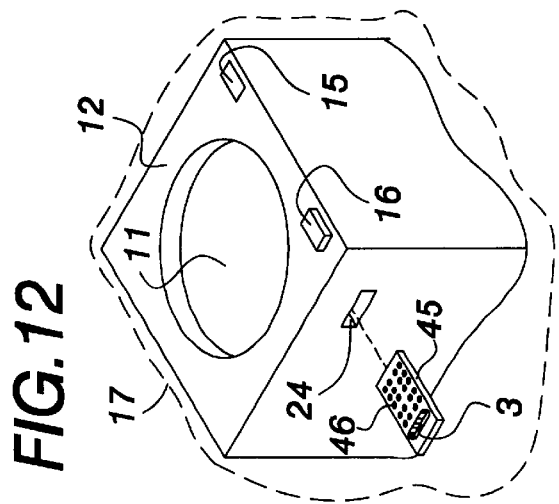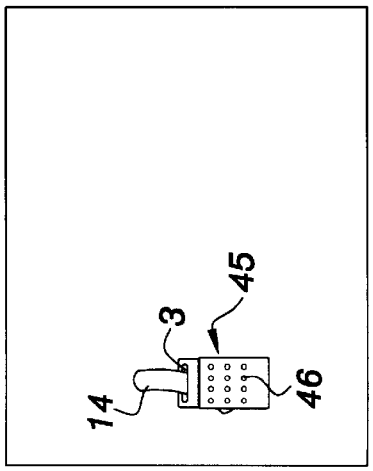

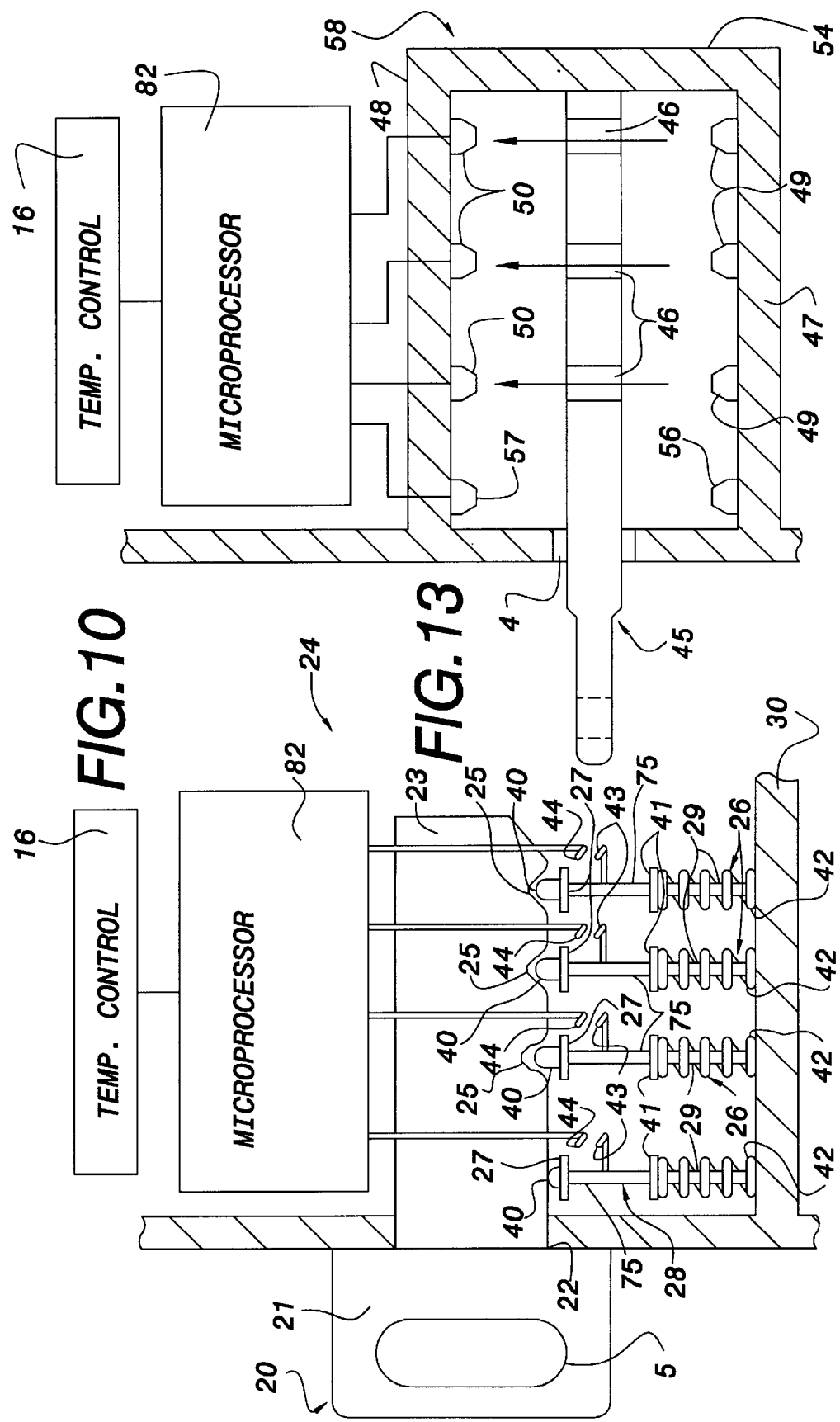

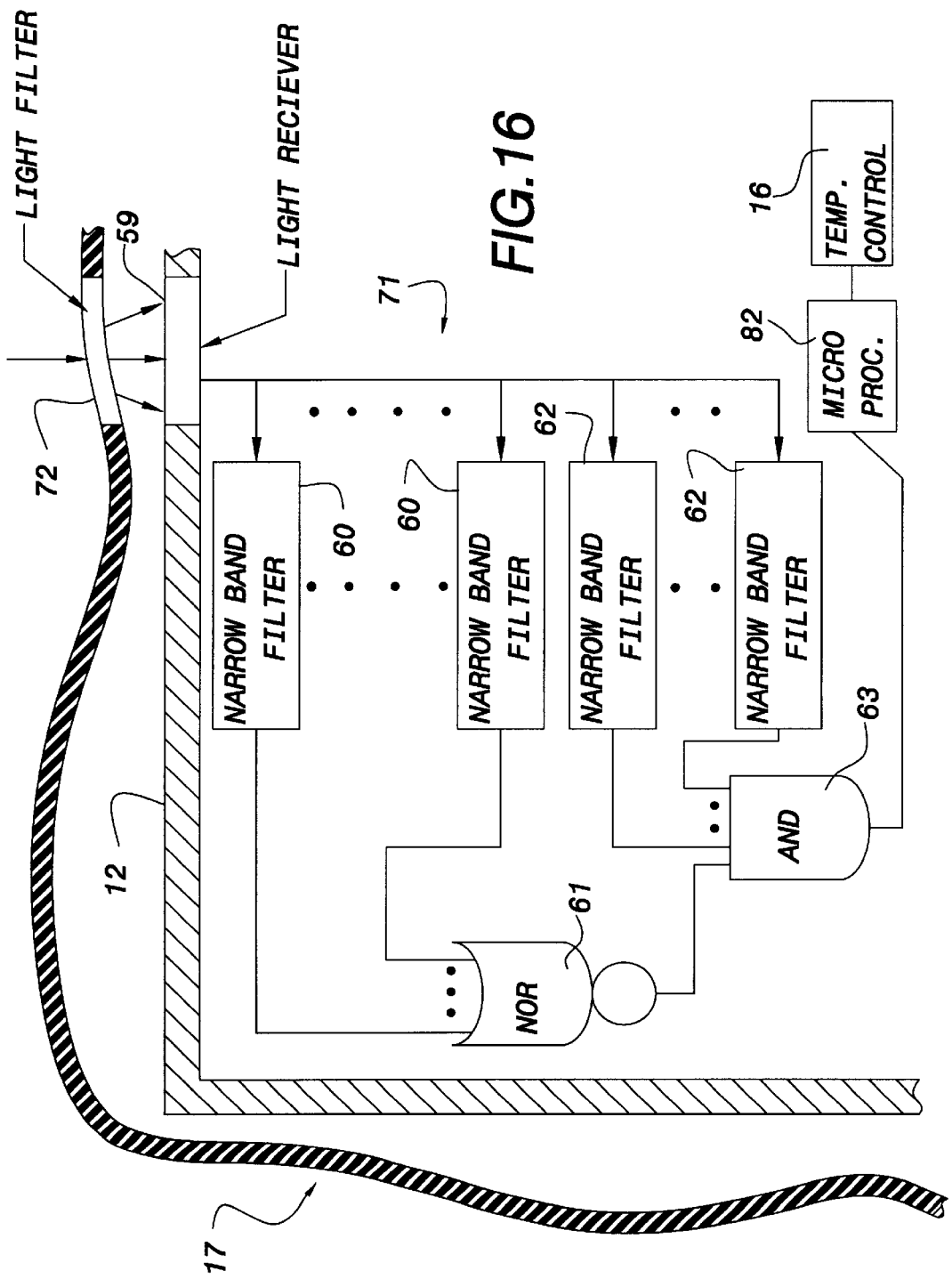

METHOD AND APPARATUS FOR ENSURING STERILITY OF SURGICAL DRAPES USED WITH SURGICAL EQUIPMENT

CROSS-REFERENCE TO RELATED APPLICATIONS

This application is a continuation-in-part of U.S. patent application Ser. No. 08/427,938, entitled "Method and Apparatus for Ensuring Sterility of Surgical Drapes Used with Surgical Equipment", filed Apr. 26, 1995, now U.S. Pat. No. 5,653,938. The disclosure of that patent application is incorporated herein by reference in its entirety.

BACKGROUND OF THE INVENTION

1. Technical Field

The present invention pertains to improvements in methods and apparatus for heating or cooling sterile surgical liquids and collecting surgical sterile slush. In particular, the invention is an improvement of the methods and apparatus disclosed in U.S. Pat. Nos. 4,393,659 (Keyes et al), 4,934,152 (Templeton), 5,163,299 (Faries, Jr. et al), 5,331,820 (Faries, Jr. et al), 5,333,326 (Faries, Jr. et al) and 5,457,962 (Faries, Jr. et al). The disclosures in those patents are expressly incorporated herein by reference in their entireties.

2. Discussion of the Prior Art

The above-referenced Keyes et al U.S. Pat. No. (4,393,659) discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton U.S. Pat. No. (4,934,152), the Keyes et al system has a number of disadvantages. In particular, the separate product basin must be removed and re-sterilized after each use. Additionally, the glycol or other thermal transfer medium is highly flammable or toxic and, in any event, complicates the procedure. The Templeton patent discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al U.S. Pat. No. (5,163,299) notes that scraping congealed liquid from the drape is undesirable in view of the potential for damage to the drape, resulting in a compromise of sterile conditions. As a solution to the problem, the Faries, Jr. et al U.S. Pat. No. (5,163,299) proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel.

The Faries, Jr. et al U.S. Pat. No. (5,331,820) resolves the problem of manual manipulation of the drape by providing a method and apparatus to automatically remove the congealed liquid adhering to the drape without endangering the integrity of the drape. A flat disk or plate is provided at the bottom of the basin under the drape. The plate is moved in an up and down manner to manipulate the drape and disengage the congealed liquid adhering to the drape. The plate may be attached to a mechanism below the basin, or to the drape itself as disclosed in the Faries, Jr. et al U.S. Pat. No. (5,457,962).

The Templeton U.S. Pat. No. (4,934,152) further provides an electrical heater disposed at the bottom of the basin to convert the sterile slush to warmed liquid, or to heat additional sterile liquid added to the basin. Templeton describes the need for such warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both the sterile warmed liquid and the sterile surgical slush. Accordingly, the Faries, Jr. et al U.S. Pat. No. (5,333,326) provides a method and apparatus for simultaneously providing surgical slush and warmed surgical liquid in separate basins during a surgical procedure using a single drape forming a drape receptacle within each basin.

The apparatus disclosed in the foregoing patents may stand some improvements to further ensure sterile conditions. Specifically, a sterile drape is typically disposed over a thermal treatment system having a basin recessed in a top surface of the system housing wherein a portion of the drape is pushed down into and conforms to the basin to form a drape container or receptacle for containing a sterile medium. The drape essentially forms a sterile field above the basin to maintain sterility of the sterile medium. Since the sterile surgical drape provides a sterile field above the basin for the sterile medium, it is important that a sterile drape be used for each procedure during system operation in order to prevent contamination of the sterile medium and serious injury to a patient. Although operating room personnel can be advised and cautioned about the importance of placing a drape over a thermal treatment system prior to the performance of a surgical procedure, there is no assurance that carelessness will not result in operation of a thermal treatment system without the use of a drape and thereby compromise the sterile field of an entire surgical procedure. Thus, it is desirable to ensure sterility of the sterile medium by enabling operation of the thermal treatment system only when a sterile surgical drape is positioned on the thermal treatment system.

Although the thermal treatment system disclosed in U.S. Pat. No. 5,653,938 identifies previously used drapes to control thermal treatment system operation by detecting a bar code affixed to or imprinted on drapes, the bar code identification is typically used only for drape detection purposes, thereby restricting bar code utilization potential. Further, since the bar code is affixed to or imprinted on the drape, the bar code is typically transferred onto material (e.g., drape material) that may not be optimal for containing the bar code, thereby possibly distorting the bar code and increasing the likelihood of erroneous identification. Accordingly, the bar code system disclosed in the aforementioned copending application may stand some improvement to further utilize the bar code identification for performance of various tasks, such as drape inventory, and to further dispose the bar code on a tag for attachment to the drape wherein the tag includes material (e.g., paper, cardboard, etc.) for containing the bar code that is conducive to proper bar code identification. Thus, there exists a need in the art for a thermal treatment system to ensure sterility of a sterile medium contained within a thermal treatment system basin by utilizing improved drape detection techniques that generally employ different types of drape indicators to detect the presence of the drape on the thermal treatment system in order to control thermal treatment system operation.

OBJECTS AND SUMMARY OF THE INVENTION

Accordingly, it is an object of the present invention to automatically ensure the sterility of a sterile medium contained within a thermal treatment system basin by enabling operation of the thermal treatment system upon detection of a sterile surgical drape positioned over the thermal treatment system wherein the drape provides a sterile field above the basin to maintain sterility of the sterile medium.

It is another object of the present invention to detect the presence of a sterile surgical drape on a thermal treatment system to ensure sterility of a sterile medium contained within a thermal treatment system basin by verifying a bar code attached to the drape wherein a bar code reader disposed within the thermal treatment system enables thermal treatment system operation in response to identification of the drape bar code. Further, the bar code may be utilized to maintain information related to the drape for performing various tasks, such as drape inventory.

Yet another object of the present invention is to detect the presence of a sterile surgical drape on a thermal treatment system to ensure sterility of a sterile medium contained within a thermal treatment system basin by verifying a mechanical key attached to the drape wherein an electromechanical tumbler disposed within the thermal treatment system enables thermal treatment system operation in response to proper verification of the mechanical key.

Still another object of the present invention is to detect the presence of a sterile surgical drape on a thermal treatment system to ensure sterility of a sterile medium contained within a thermal treatment system basin by verifying an optical key attached to the drape wherein an optical key reader disposed within the thermal treatment system enables thermal treatment system operation in response to proper verification of the optical key.

A further object of the present invention is to detect the presence of a sterile surgical drape on a thermal treatment system to ensure sterility of a sterile medium contained within a thermal treatment system basin by verifying specific bands or colors of light passed by a light filter attached to the drape wherein light band filter circuitry disposed within the thermal treatment system enables thermal treatment system operation in response to proper verification of the light bands.

Yet another object of the present invention is to detect the presence of a sterile surgical drape on a thermal treatment system to ensure sterility of a sterile medium contained within a thermal treatment system basin by detecting light directed from a light source disposed within the thermal treatment system toward reflective material either attached to the drape or used for construction of the drape itself wherein a light detector disposed within the thermal treatment system enables thermal treatment system operation in response to detecting the reflected light.

Still another object of the present invention is to detect the presence of a sterile surgical drape on a thermal treatment system to ensure sterility of a sterile medium contained within a thermal treatment system basin by detecting either magnetic media attached to the drape or a magnetic pigment or resin additive incorporated within the drape material wherein magnetic detectors disposed within the thermal treatment system enable thermal treatment system operation in response to detecting the magnetic media or magnet pigment.

The aforesaid objects are achieved individually and in combination, and it is not intended that the present invention be construed as requiring two or more of the objects to be combined unless expressly required by the claims attached hereto.

According to the present invention, a thermal treatment system and corresponding sterile surgical drape include a variety of mechanisms to ensure sterility of a sterile medium contained within a thermal treatment system basin. The mechanisms enable operation of the thermal treatment system only upon detecting the sterile surgical drape positioned on the thermal treatment system wherein the drape provides a sterile field above the basin to maintain sterility of the sterile medium. Initially, a bar code reader is disposed within a thermal treatment system to detect the presence of a bar code attached to a sterile drape placed on that system in substantially the same manner disclosed in copending U.S. patent application Ser. No. 08/427,938. The bar code is disposed on a tag or card that is attached to the drape wherein thermal treatment system operation is enabled upon detecting the bar code and verifying that the bar code is associated with a sterile drape. The bar code may be further utilized to maintain other information related to the drape to perform various tasks, such as drape inventory.

A mechanical key may similarly be attached to a sterile surgical drape to indicate the presence of the drape on a thermal treatment system and enable thermal treatment system operation. Specifically, the mechanical key includes a plurality of indentations along a key edge that define a particular pattern representing a drape identification. A key receptacle for receiving and verifying the mechanical key is incorporated into the thermal treatment system and includes an electromechanical tumbler. The tumbler includes a plurality of plungers to sense the key indentations and to ascertain and verify the drape identification. When the drape is placed onto the system, the mechanical key is inserted into the key receptacle to enable the tumbler to verify the mechanical key in order to determine drape presence on the system and initiate thermal treatment system operation. Alternatively, an optical key may be utilized to indicate drape presence on the thermal treatment system. The optical key includes an array of openings defining a particular pattern that represents a drape identification. An optical key receptacle for receiving and verifying the optical key is incorporated into the thermal treatment system and includes an optical key reader. The reader includes light sources and detectors to sense the optical key openings and to ascertain and verify the drape identification. When the drape is placed onto the system, the optical key is inserted into the optical key receptacle to enable the reader to verify the optical key in order to determine drape presence on the system and initiate thermal treatment system operation.

Drape detection may further be accomplished via a light filter patch attached to the drape that passes specific bands or colors of light to a light receiver and associated light band filter circuitry disposed within the thermal treatment system. The drape is placed over the thermal treatment system such that the light filter patch is coincident the light receiver. The light band filter circuitry includes a plurality of narrow band filters that are configured to detect a particular band of light. The light band filter circuitry detects the presence of the drape on the system and enables thermal treatment system operation when only the specific bands of light passed by the light filter patch are received by the light receiver. Further, light may be alternatively utilized to indicate drape presence on a thermal treatment system wherein reflective material may be attached to the drape, or used for construction of the drape itself. A light source and light detector arrangement is disposed within the thermal treatment system wherein the drape is placed over the thermal treatment system such that reflective material is coincident the light source and light detector arrangement. The light source and detector may be respectively configured to emit and detect a particular band or color of light. Light emitted from the light source is reflected by the reflective material toward the light detector to indicate the presence of the drape on the thermal treatment system. Upon detecting light having the particular band of the light source and an intensity sufficient to exceed a predetermined threshold, the light detector enables thermal treatment system operation.

The presence of a drape on the thermal treatment system may also be detected via magnetic media. Specifically, magnetic media may be disposed within or attached to the drape or a magnetic pigment or resin additive may be incorporated into the drape material. Magnetic detectors are disposed within the thermal treatment system wherein the drape is placed over the thermal treatment system such that the magnetic media or magnetic pigment or resin additive are detectable by the magnetic detectors. The magnetic detectors sense the magnetic media or magnetic pigment or resin additive to detect the presence of the drape on the thermal treatment system and to enable thermal treatment system operation.

The above and still further objects, features and advantages of the present invention will be apparent upon consideration of the following detailed description of the specific embodiments thereof, particularly when taken in conjunction with the accompanying drawings wherein like reference numerals in the various figures are utilized to designate like components.

BRIEF DESCRIPTION OF THE DRAWINGS

FIG. 8 is a top view in plan of a surgical drape including a mechanical key for indicating the presence of the drape on a thermal treatment system according to another embodiment of the present invention.

FIG. 9 is an exploded view in perspective of the surgical drape of FIG. 8 placed over a thermal treatment system having a key receptacle including a tumbler for receiving and verifying the mechanical key to determine the presence of the drape on the thermal treatment system and to enable thermal treatment system operation.

FIG. 10 is a side view in elevation and partial section of the thermal treatment system of FIG. 9 schematically illustrating the thermal treatment system tumbler mechanism for verifying the drape mechanical key and enabling thermal treatment system operation.

FIG. 11 is a top view in plan of a surgical drape having an optical key for indicating the presence of the drape on a thermal treatment system according to yet another embodiment of the present invention.

FIG. 12 is an exploded view in perspective of the surgical drape of FIG. 11 placed over a thermal treatment system having an optical key reader for receiving and verifying the optical key to determine the presence of the drape on the thermal treatment system and to enable thermal treatment system operation.

FIG. 13 is a side view in elevation and partial section of the thermal treatment system of FIG. 12 schematically illustrating the thermal treatment system optical key reader for verifying the drape optical key and enabling thermal treatment system operation.

FIG. 14 is a top view in plan of a surgical drape having a light filter patch for passing specific bands or colors of light that indicate the presence of the drape on a thermal treatment system according to still another embodiment of the present invention.

FIG. 15 is an exploded view in perspective of the surgical drape of FIG. 14 placed over a thermal treatment system having a light receiver and light band filter circuitry for receiving and verifying the light bands passed by the drape light filter patch to determine the presence of the drape on the thermal treatment system and to enable thermal treatment system operation.

FIG. 16 is a side view in elevation and partial section of the thermal treatment system of FIG. 15 schematically illustrating the light band filter circuitry for verifying the light bands passed by the drape light filter patch and enabling thermal treatment system operation.

DESCRIPTION OF THE PREFERRED EMBODIMENTS

The present invention can be applied to various apparatus for providing thermally treated sterile media such as surgical slush machines, liquid warming and cooling systems, and multiple unit machines capable of performing both liquid warming, cooling and slush generation.

Figure 1:
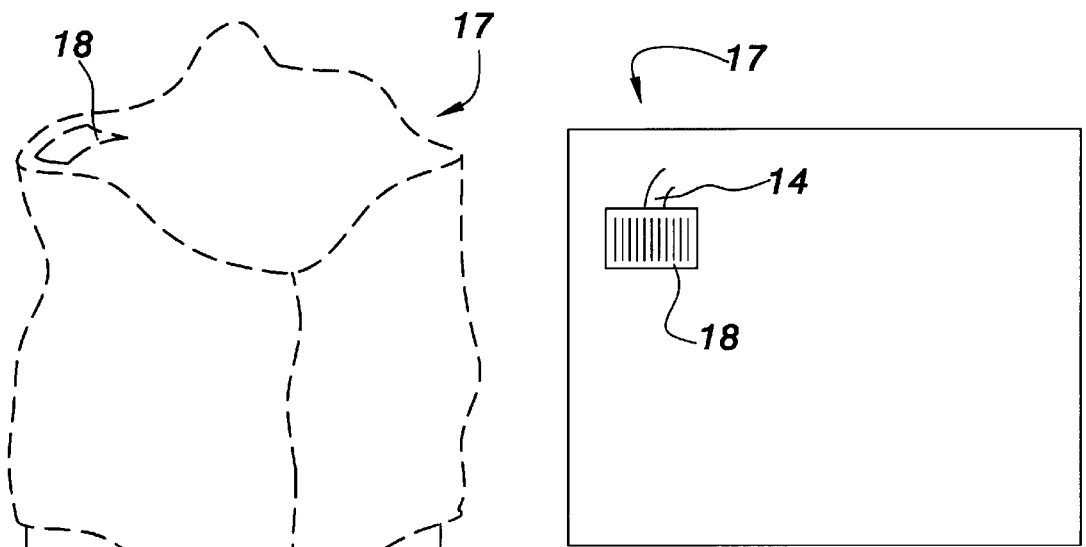
FIG. 1 is a top view in plan of a surgical drape having a tag including a bar code identifying the drape according to an embodiment of the present invention.
Figure 2:
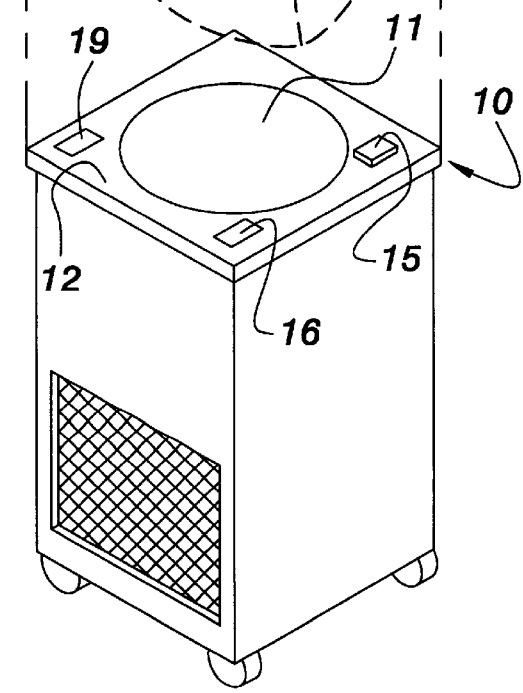
FIG. 2 is an exploded view in perspective of the surgical drape of FIG. 1 placed over a thermal treatment system having a bar code reader for ascertaining the bar code to determine drape sterility.

FIGS. 1–2 illustrate an example of a thermal treatment system and surgical drape for detecting the presence of the drape on the system and determining drape sterility according to an embodiment of the present invention. The thermal treatment system, by way of example, produces surgical slush and includes a cabinet 10 with a top surface 12 having a basin 11 mounted thereon in an appropriately sized recess. Basin 11 is made of thermally conductive material, typically stainless steel, and includes a generally flat bottom wall and a frusto-conical sidewall. A conventional refrigeration unit (not shown) is disposed within cabinet 10 and typically includes a compressor, a condenser and an expansion control unit connected by appropriate fluid conduits in a closed refrigeration loop with an evaporator (not shown). The evaporator is in the form of a coil wound about the exterior surface of basin 11 in thermal transfer relation therewith. When the refrigeration unit is activated via appropriate controls 15 and temperature control 16, the evaporator cools the sidewall of basin 11 to a temperature substantially below the freezing temperature of the liquid used in forming the sterile slush. This temperature is preferably on the order of −32° F. to 10° F. For further details of the structure and operation of the refrigeration unit, reference is made to the aforementioned Keyes et al and Templeton patents. A sterile surgical drape 17, preferably transparent, is disposed over the top and sides of cabinet 10 and made to conform to the side wall and bottom of basin 11. The portion of surgical drape 17 disposed in the basin serves as a sterile receptacle or container for sterile liquid placed therein to be cooled to the desired sterile slush consistency. Typical sterile liquid used by thermal treatment systems (i.e., systems that warm, cool or congeal sterile liquid) is a 0.80% to 0.95% sodium chloride solution (i.e., saline).

The drape illustrated in FIG. 2 is of the fitted type (i.e., contoured and seamed to fit to the cabinet). It is to be understood that the present invention equally applies to non-fitted drapes that simply hang loosely over the cabinet sides.

Drape 17 contains a bar code tag 18 typically disposed at any location on the non-sterile surface of the drape for positioning over a bar code reader socket or window 19. Bar code reader socket 19 is typically disposed within cabinet top surface 12, however, the socket may be disposed anywhere on the thermal treatment system capable of enabling the socket to ascertain the drape bar code. The bar code retrieved by the bar code reader is utilized to check drape sterility in order to control electrical power application to temperature controller 16. The bar code is permanently affixed to or imprinted on the tag in any suitable manner, while the tag may include any material capable of containing the bar code (e.g., paper, cardboard, etc.) and may be affixed to the drape via a band 14 or any other fastening techniques (e.g., string, chain, directly attached or mounted on the drape via adhesives, etc.). Band 14 may be attached to the drape via any suitable adhesive, while the tag may be engaged by the band in any manner capable of securing the tag to the drape. The bar code and tag are typically attached to the drape at the time the drape is manufactured.

When the thermal treatment system is operating, the sterile liquid in the drape receptacle freezes in pieces on the surgical drape covering the sidewalls of the basin. The thermal treatment system may further include a dislodgement mechanism for automatically removing frozen pieces of the sterile liquid from the surgical drape covering the basin walls to form the sterile slush. The dislodgement mechanism may be of the types disclosed in the aforementioned patents and copending application. For example, the dislodgement mechanism of the copending application includes a motor that reciprocates a shaft up and down wherein the shaft extends from the motor to a plate disposed at the bottom of the basin beneath the drape receptacle. The shaft, in turn, moves the plate up and down, wherein the plate moves the bottom of the drape receptacle up and down to loosen attached pieces of frozen saline. For further details on the operation of this and other types of dislodgement mechanisms, reference is made to U.S. Pat. No. 5,653,938 and the aforementioned patents.

Figure 3:
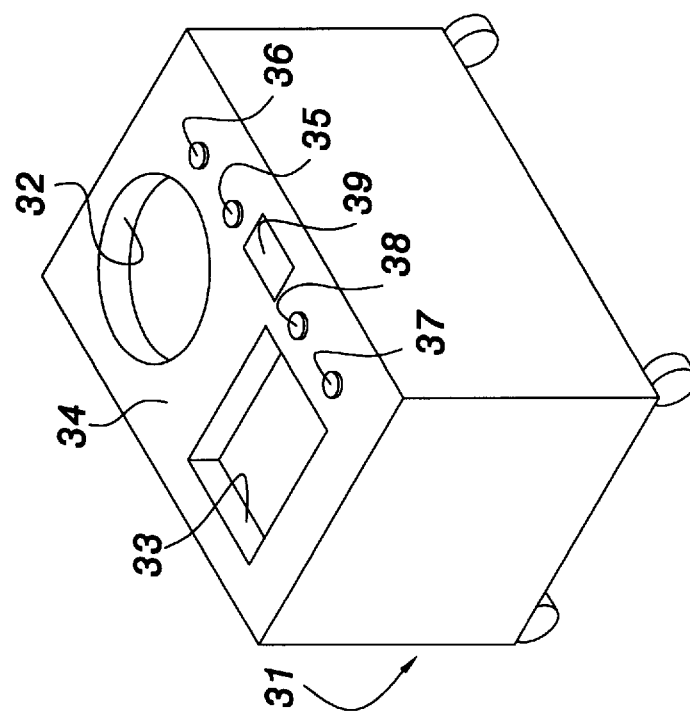
FIG. 3 is a view in perspective of a multiple basin thermal treatment system of the type employed by the present invention for heating and cooling a sterile medium.

Referring to FIG. 3, there is illustrated an example of a thermal treatment system containing both a slush generating unit and a sterile liquid warming unit. Specifically, an integral assembly 31 includes a cooling basin 32 for producing surgical slush and a warming basin 33 for heating sterile liquid wherein each basin is recessed into a top surface 34 of a common cabinet. Also disposed on top surface 34 are cooling unit power switch 35, a cooling unit temperature controller/indicator 36, a heater power switch 37, a heater unit temperature controller/indicator 38, and a bar code reader socket or window 39.

Figure 4:
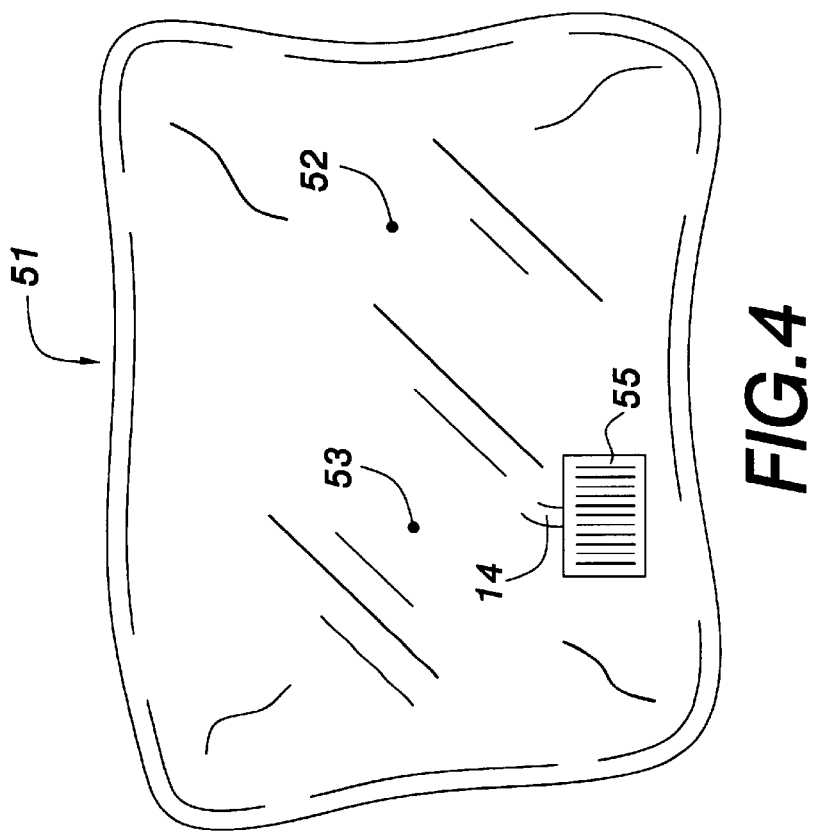
FIG. 4 is a top view in plan of a surgical drape for the multiple basin thermal treatment system of FIG. 3 having a tag including a bar code identifying the drape.

A sterile surgical drape 51 suitable for covering the entire top surface 34 to provide drape receptacles for both basins 32 and 33 is illustrated in FIG. 4. Drape 51 has bar code tag 55, substantially similar to the bar code tag described above, including a bar code affixed, imprinted or otherwise attached thereto for use in determining drape presence and sterility as described below. The bar code tag is typically disposed on the non-sterile surface of the drape via a band 14 as described above for the drape of FIG. 1, however, the bar code may be disposed anywhere on the drape that enables the tag to be read by a bar code reader. Drape 51 may include two centering marks or indicia 52, 53 adapted to be placed over the centers of the cooling and heating basins 32 and 33, respectively, during installation of the drape on the system.

Figure 5:
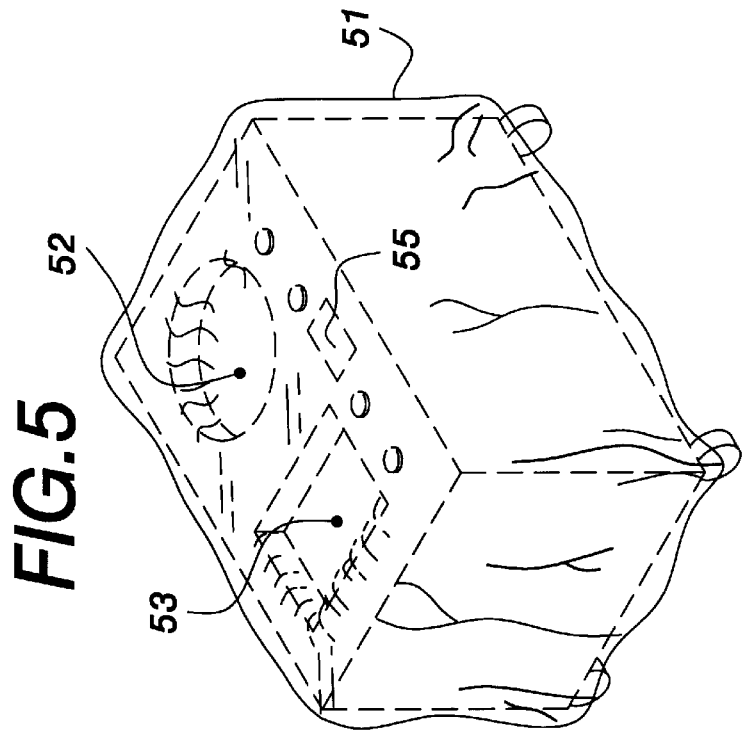
FIG. 5 is a view in perspective of the surgical drape of FIG. 4 deployed on the thermal treatment system of FIG. 3.

FIG. 5 illustrates centering indicia 52, 53 properly positioned when drape 51 is pushed down into respective basins until the drape conforms to the basin shapes. Bar code tag 55 is manipulated such that the bar code tag is positioned over bar code reader socket 39 (FIG. 3) to enable determination of the drape's presence and sterility as described below.

The surgical drapes for the above described thermal treatment systems are typically made of material that is impervious to heated liquid and cooled slush, and is sufficiently soft and flexible to conform to the basin walls. Typically, by way of example only, the surgical drapes are made of materials commonly used in hospitals for surgical drapes. The drapes may also be made of polyurethane film as disclosed for the surgical drape in the aforementioned Templeton patent. The surgical drapes are designed to be disposable after a single use and are provided pre-sterilized and pre-packaged in a leakproof plastic bag or other sealed container to preserve the sterile nature of the surgical drape during storage.

Figure 6:
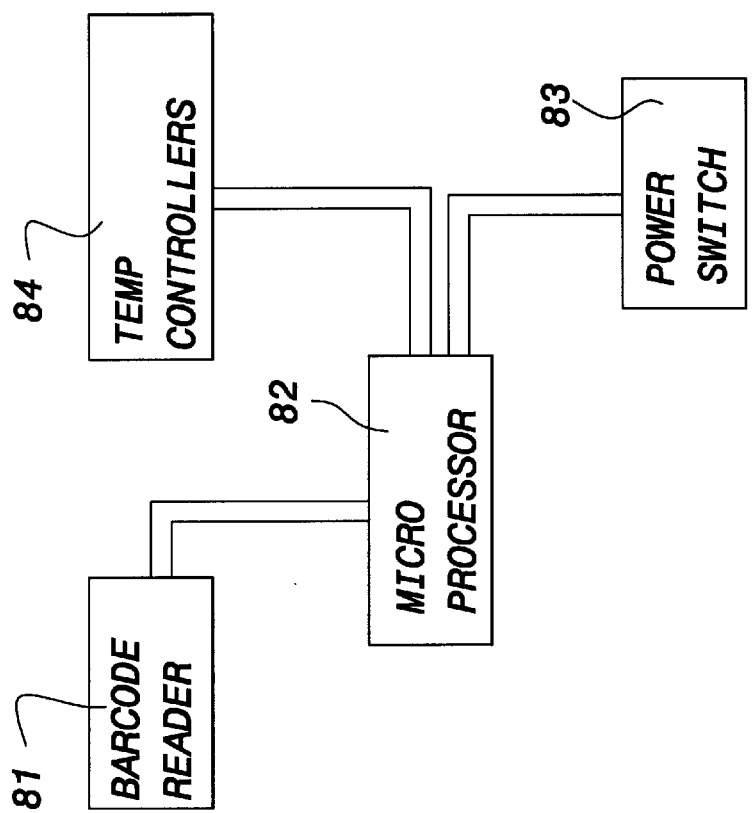
FIG. 6 is a schematic illustration of a sterile drape determination circuit.
Figure 7:
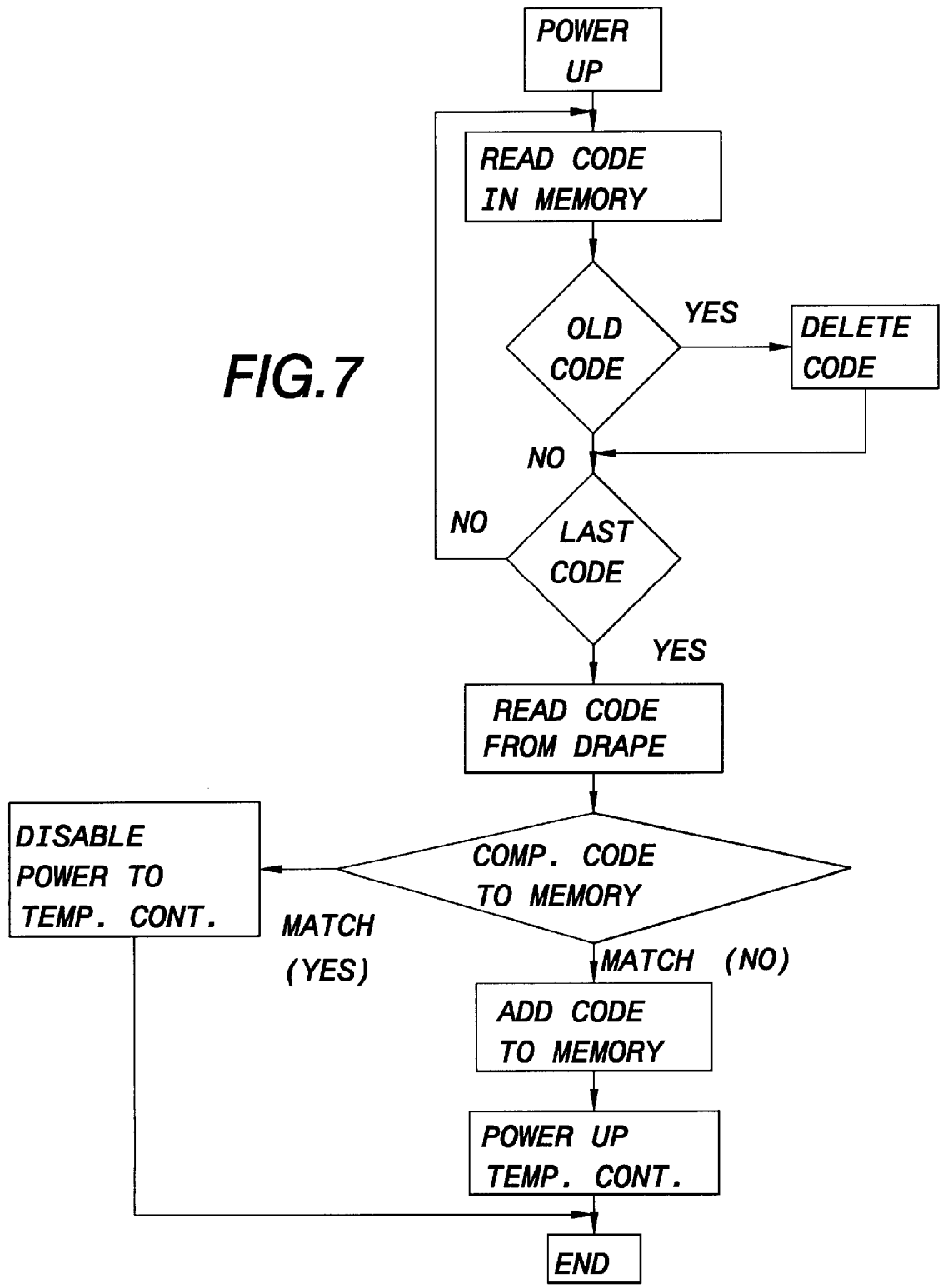
FIG. 7 is a procedural flowchart of the operation of the sterile drape determination circuit of FIG. 6.

Referring to FIG. 6, a sterile drape determination circuit may be embodied in each of the various systems described above. The sterile drape determination circuit includes a conventional bar code reader 81 which reads or senses the bar code disposed on the bar code tag attached to the surgical drape. Bar code reader 81 is typically disposed beneath the bar code reader window or inserted into the bar code reader socket. Microprocessor 82 compares the sensed bar code to previously used surgical drape bar codes stored in the microprocessor memory to determine if that bar code has been previously sensed, indicating that the surgical drape has already been used. Microprocessor 82 is connected to power switch 83 and to various temperature controllers/indicators 84 of respective warming, cooling and slush generation units wherein the microprocessor controls operation of these temperature controllers as described below. Operation of the sterility circuit is described immediately below with reference to FIG. 7.

On power up of the system, the microprocessor conserves memory by deleting older stored bar codes of previously used drapes which have been in storage longer than a predetermined time period. Next, the bar code reader ascertains the bar code of the surgical drape currently being used. The ascertained bar code is sent to the microprocessor to determine if the current surgical drape bar code resides in memory indicating that the surgical drape has been previously used and is therefore not sterile. If there is no match, the microprocessor adds the current surgical drape bar code to memory and enables the temperature controllers to operate their respective temperature control units. If a match was found, then the surgical drape is deemed non-sterile because of prior use and the microprocessor disables power to the temperature controllers to prevent operation with a non-sterile drape.

Microprocessor control is accomplished by software providing the data comparisons and old data deletions. The microprocessor can be implemented by virtually all commercially available microprocessor chips as known in the art, general circuitry, combinational logic or any other switching devices capable of controlling power to a device. Further, the microprocessor or other external computer systems may utilize the drape bar code to maintain information about the drapes to perform various drape management tasks. For example, the drape bar code may be utilized to maintain inventory information relating to the quantity and types of drapes that are available for use at a particular facility. Moreover, the drape bar code may be utilized to maintain information associated with the drape, such as the particular department or location where the drape resides, drape costs and age of the drapes. It is to be understood that any information relating to a particular drape may be maintained within the microprocessor and/or external computer system wherein the bar code is utilized as a key or index to associate the information with a particular drape.

Ensuring sterility of the sterile liquid may also be accomplished by controlling power to a thermal treatment system based on whether or not other indicia or identifying objects (e.g., a mechanical or optical key) disposed on a drape are detected and/or verified. The drape is typically positioned on the system with the indicia or identifying object located adjacent or inserted within a compatible reader. The reader attempts to detect and/or verify the indicia or identifying object and sends a signal to a microprocessor, based on the detection and/or verification, indicating whether or not the indicia or identifying object, and hence, the drape is present. The microprocessor then controls power to the system based on that signal. Various embodiments for this type of configuration are described below. The indicia or identifying objects utilized to indicate drape presence include mechanical or optical keys, light filters passing specific bands or colors of light, light sources reflecting light from the drape toward light detectors, and magnetic indicia, however, any other indicia or identifying objects capable of drape recognition may be used wherein some indicia disposed on every drape may be identical.

A surgical drape having a mechanical key to indicate the presence of the drape on a thermal treatment system and enable thermal treatment system operation is illustrated in FIG. 8. Specifically, drape 17 is substantially similar to the bar code drape described above for FIG. 1 except that the drape includes a mechanical key 20 preferably disposed on the non-sterile side of the drape. Mechanical key 20 is similar to conventional mechanical keys and may be attached to the drape via a band 14 or by any other fastening techniques (e.g., string, chain, directly fastened to or mounted on the drape via adhesives or ultrasonic welding, etc.). Band 14 may be attached to the drape via any suitable adhesive, while the mechanical key may be engaged by the band in any manner capable of securing the mechanical key to the drape. Mechanical key 20 includes a substantially rectangular handle or gripping portion 21 disposed at the key proximal end and an elongated substantially rectangular stem 23 extending from the approximate center of the handle distal edge wherein the handle proximal and distal edges typically extend along the longer handle dimension. Handle 21 preferably includes a substantially elliptical opening having a major axis extending along the longer handle dimension. Opening 5 is disposed toward the handle proximal end wherein the opening is of sufficient size to enable band 14 to traverse the opening and secure mechanical key 20 to the drape. It is to be understood that the key handle, stem and opening may be of any size or shape and may be oriented in any fashion capable of securing the key to the drape and indicating drape presence to the thermal treatment system as described below. In addition, the mechanical key may be disposed anywhere on the drape capable of enabling insertion of the key within the key receptacle.

Mechanical key 20 typically includes a plurality of coded indentations or notches 25 of varying depths defined toward the stem distal end in a stem edge extending along the longer stem dimension. The depths and/or shapes and/or positions of indentations collectively form a code pattern that identifies mechanical key 20 and drape 17 to a thermal treatment system as described below. Indentations 25 each typically include oppositely angled edges that form a rounded indentation apex or peak, while the distal stem corner adjacent indentations 25 is cut-off or angled wherein the shape of the indentations in combination with the angled stem corner facilitate entry and removal of the mechanical key from the thermal treatment system as described below. However, any quantity or shape of indentations 25 capable of entry and removal of the mechanical key from the thermal treatment system may be utilized to form the indentation pattern.

Drape 17 is placed over a thermal treatment system wherein a portion of the drape is pushed down into and conforms to the basin to form a drape receptacle as described above. Mechanical key 20 is inserted into a substantially rectangular key receptacle described below such that the mechanical key is preferably oriented with the longer dimension of the key handle being substantially vertical and the stem edge containing indentations 25 facing downward. The key receptacle is disposed within a cabinet sidewall of the thermal treatment system to enable system operation wherein the key receptacle is oriented with its longer dimension substantially vertical to accommodate the mechanical key. The mechanical key and key receptacle may be oriented in any fashion capable of permitting insertion of the key into the receptacle for identification of the drape by the thermal treatment system. For example, the receptacle may be disposed in the top surface 12 of the cabinet, and the key may be positioned on the drape accordingly.

An exemplary thermal treatment system for utilizing mechanical key drape 17 is illustrated in FIGS. 9–10. Specifically, the thermal treatment system is substantially similar to the bar code thermal treatment system described above for FIG. 2 except that the thermal treatment system includes a key receptacle 22 and an electromechanical tumbler 24. Key receptacle 22 includes dimensions slightly larger than the transverse cross-section of the mechanical key stem such that the key handle abuts the cabinet sidewall to enable insertion of only the key stem within the key receptacle. Key receptacle 22 is disposed and oriented within a cabinet sidewall as described above for receiving mechanical key 20, and extends into electromechanical tumbler 24 disposed adjacent the key receptacle within the system cabinet interior. Tumbler 24 includes a plurality of plungers 26 that sense indentations 25 defined within mechanical key 20 wherein each plunger generates a signal for transmission to a microprocessor 82 enabling the microprocessor to determine whether or not the appropriate mechanical key has been inserted into the tumbler. An additional plunger 28, disposed toward key receptacle 22, senses the presence of mechanical key 20 within tumbler 24 and generates a corresponding signal for transmission to microprocessor 82. A cabinet interior ledge 30 extends beneath key receptacle 22 from the cabinet sidewall housing that key receptacle wherein each plunger 26, 28 includes a guide rod 29 extending from the ledge. Guide rods 29 of plungers 26, 28 are typically substantially cylindrical, but may be of any shape, and extend substantially parallel to each other from ledge 30 toward key receptacle 22. The length of guide rods 29 is typically less than the distance between the key receptacle 22 and ledge 30. Detector rods 75 are disposed toward the distal ends of guide rods 29 of plungers 26, 28 wherein the detector rods are substantially cylindrical and hollow. A support flange 41 is disposed at the proximal end of respective detector rods 75 of plungers 26, 28. Support flange 41 is typically a substantially annular disk having an opening with dimensions substantially similar to the cross-sectional diameter of a respective detector rod 75. Each detector rod 75 is preferably attached to the approximate center of a corresponding support flange such that a channel extends form support flange 41 through the hollow interior of that detector rod. The cross-sectional diameter of respective detector rods 75 is slightly greater than the cross-sectional diameter of corresponding guide rods 29 such that the detector rods are disposed over and receive the guide rods within the detector rod channels. In other words, detector rods 75 are disposed over a distal portion of guide rods 29 in sliding relation such that the guide rods direct detector rod motion. Detector rods 75 may be of any length capable of receiving sufficient portions of corresponding guide rods 29 within the respective detector rod channels to enable guide rods 29 to guide detector rod motion.

A stop flange 27 and piston 40 are disposed on the distal end of each detector rod 75 of plungers 26, 28 wherein piston 40 is disposed distally of the stop flange. Stop flange 27 is typically a substantially circular disk wherein each detector rod 75 is preferably attached to the approximate center of a respective stop flange. The diameter of each stop flange 27 of plungers 26 is slightly greater than the width of a corresponding indentation 25 to prevent plungers 26 from overextending into the indentations and inhibiting movement of the key during traversal of the key receptacle. Pistons 40 each extend from a receptive stop flange 27 of plungers 26, 28 toward key receptacle 22 and are each substantially cylindrical having a tapered rounded distal end for insertion into indentations 25 defined within mechanical key 20.

A helical spring 42 is disposed around the proximal portion of each guide rod 29 between support flange 41 and ledge 30 wherein the spring exerts force on each support flange 41 to bias detector rods 75 and pistons 40 toward a mechanical key 20 inserted within tumbler 24. However, any other springs or biasing mechanisms may be utilized to bias the detector rods toward the key. Detector rods 75 of plungers 26, 28 each further include a plunger contact 43 transversely extending from the approximate center of each detector rod for connection with a corresponding mated microprocessor contact 44 connected to microprocessor 82. Alternatively, plunger contacts 43 may extend from any portions of respective detector rods 75 capable of enabling the plunger contacts to interface corresponding microprocessor contacts 44. Plunger contacts 43 typically include or are connected to a voltage source (not shown) of sufficient voltage such that when a particular plunger contact 43 interfaces a corresponding microprocessor contact 44, microprocessor 82 receives a high level logic signal (i.e., a logic or binary one signal) associated with that plunger. Conversely, microprocessor 82 receives a low level logic signal (i.e., a logic or binary zero signal) associated with a particular plunger when a corresponding plunger contact 43 does not interface an associated microprocessor contact 44.

When mechanical key 20 is inserted into tumbler 24, pistons 40 of plungers 26 are biased toward corresponding indentations 25 via springs 42, thereby enabling the plungers to ascertain the indentation pattern identifying the drape. When indentations 25 are of sufficient depth, corresponding plunger contacts 43 interface microprocessor contacts 44, thereby sending associated high level logic signals to microprocessor 82 to enable the microprocessor to verify the mechanical key. Specifically, indentations 25 typically include oppositely angled edges forming a rounded peak as described above to enable pistons 40 to traverse the indentations as mechanical key 20 is inserted into and removed from tumbler 24. Indentations 25 are typically of varying depths such that only certain keys enable particular plunger contacts 43 to interface microprocessor contacts 44 and permit microprocessor 82 to enable operation of the system. When an indentation includes sufficient depth, a corresponding piston 40 enters that indentation a sufficient distance to enable plunger contact 43 to interface a corresponding microprocessor contact 44 associated with that plunger. However, when an indentation includes an insufficient depth, a corresponding piston 40 enters that indentation and typically abuts the indentation peak wherein the indentation peak opposes the bias exerted on piston 40 by spring 42 and prevents plunger contact 43 form interfacing a corresponding microprocessor contact 44 associated with that plunger. Microprocessor 82 essentially receives low level logic signals from plungers that do not sense an indentation (i.e., a plunger contact 43 not interfacing a microprocessor contact 44), while plungers that sense an indentation (i.e., a plunger contact 43 interfacing a microprocessor contact 44) send a high level logic signal to the microprocessor. The logic signals are examined by microprocessor 82 as described below to determine the presence of a valid key within tumbler 24 and initiate thermal treatment system operation. The lengths of pistons 40 and/or detector rods 75 of plungers 26, and/or the distances between plunger contacts 43 of plungers 26 and corresponding microprocessor contacts 44 may be adjusted such that a particular plunger contact 43 associated with a plunger 26 interfaces a corresponding microprocessor contact 44 only when piston 40 is biased against a specific indentation 25. In other words, specific key indentation patterns may be sensed via the plungers by adjusting piston and/or detector rod lengths, and/or distances between plunger and microprocessor contacts.

Helical spring 42 of plunger 28 biases corresponding piston 40 against a portion of mechanical key 20, preferably containing no indentations, wherein the mechanical key opposes the spring bias to prevent plunger contact 43 of plunger 28 from interfacing a corresponding microprocessor contact 44. Microprocessor 82 consequently receives a low level logic signal associated with plunger 28 indicating the presence of a mechanical key within tumbler 24. When no key is present within tumbler 24, spring 42 of plunger 28 biases corresponding piston 40 toward key receptacle 22 as described above. However, since no key is present within tumbler 24 to oppose this bias, plunger contact 43 of plunger 28 interfaces a corresponding microprocessor contact 44, thereby sending a high level logic signal to microprocessor 82 indicating that no mechanical key is present within the tumbler.

Microprocessor 82 receives logic signals from microprocessor contacts 44 associated with plungers 26, 28 and analyzes the signals to determine the presence of an appropriate mechanical key within tumbler 24. Specifically, signals from microprocessor contacts 44 of plungers 26, 28 form a bit pattern wherein each signal from a microprocessor contact 44 corresponds to a single bit within the bit pattern. The signal from microprocessor contact 44 of plunger 28 is typically the most significant bit of the bit pattern, however, the microprocessor contact signals may be arranged in any fashion and may correspond to any of the bits within the bit pattern. The bit pattern formed from the microprocessor contact signals is compared to a predetermined bit pattern by microprocessor 82 to determine if an appropriate mechanical key is present within tumbler 24. The predetermined bit pattern generally indicates the signals required to be received from microprocessor contacts 44 of plungers 26, 28 to enable system operation wherein the most significant bit of the predetermined bit pattern typically corresponds to plunger 28 and is preferably set to zero to indicate the presence of a key within the tumbler as described above. Alternatively, the bits of the predetermined bit pattern may be arranged in any fashion capable of correspondence to plungers 26, 28 for verification of the key. The predetermined bit pattern generally represents the plunger and microprocessor contacts for each plunger 26, 28 that are required to interface (i.e., the plungers that are required to sense a mechanical key indentation) to enable system operation. For example, if each plunger 26 is required to detect a corresponding indentation 25 for proper verification of mechanical key 20, then the predetermined bit pattern includes a low level logic signal corresponding to plunger 28 indicating the presence of a key within tumbler 24 (i.e., plunger contact 43 of plunger 28 not interfacing a corresponding microprocessor contact 44) as described above, and a high level logic signal corresponding to each plunger 26 indicating detection of associated indentations (i.e., plunger contacts 43 interfacing corresponding microprocessor contacts 44 associated with those plungers). This may be represented by the binary bit pattern of '0111' (i.e., binary seven) wherein the most significant bit corresponds to plunger 28, while the remaining bits correspond to plungers 26. When signals from contacts 44 of plungers 26, 28 match corresponding bits of the predetermined bit pattern, the mechanical key is verified and system operation is enabled by microprocessor 82. The predetermined bit pattern may be configured to enable system operation for any combination of signals received from plungers 26, 28 and for any quantity of plungers 26, 28 such that various keys having different indentations 25 may be utilized with a particular thermal treatment system.

In operation, initially, drape 17 having mechanical key 20 is placed over a thermal treatment system to form a drape receptacle within a thermal treatment system basin as described above. Mechanical key 20 is inserted into key receptacle 22 and extends into tumbler 24 as described above. The positions of pistons 40 adapt to indentations 25 of the mechanical key, via the bias exerted on detector rods 75 by springs 42, as the key is inserted into key receptacle 22. When key 20 is fully inserted into tumbler 24 (i.e., key handle 21 abuts the cabinet side wall), springs 42 bias pistons 40 into corresponding indentations 25. Each indentation having a sufficient depth enables a corresponding piston to enter that indentation a sufficient distance to permit a corresponding plunger contact 43 to interface an associated microprocessor contact 44, thereby generating a high level logic signal associated with that plunger for transmission to microprocessor 82. Indentations having insufficient depth enable pistons 40 to enter those indentations and abut the indentation peaks. The indentation peaks overcome the bias of springs 42 and prevent corresponding plunger contacts 43 from interfacing microprocessor contacts 44 as described above, thereby generating low level logic signals associated with those plungers for transmission to microprocessor 82.

Piston 40 of plunger 28 is similarly biased toward mechanical key 20, however, the mechanical key overcomes the bias of spring 42 and prevents plunger contact 43 of plunger 28 from interfacing a corresponding microprocessor contact 44. A low level logic signal for that plunger is received by microprocessor 82 to indicate the presence of the mechanical key within tumbler 24. Microprocessor 82 receives the signals from plungers 26, 28 and examines the signals to verify the key and to enable thermal treatment system operation. The signals of microprocessor contacts 44 of plungers 26, 28 form a bit pattern that is compared to a predetermined bit pattern indicating the signals required to be received from plungers 26, 28 in order to initiate system operation as described above. If the bit pattern formed from the signals of microprocessor contacts 44 matches the predetermined bit pattern, microprocessor 82 enables power to temperature controller 16 to thermally treat basin 11. If the bit pattern formed from the signals of microprocessor contacts 44 of plungers 26, 28 does not match the predetermined bit pattern, microprocessor 82 does not enable or, in other words, disables power to temperature controller 16 to cease or prevent thermal treatment of basin 11.

An electronic or optical key may similarly be disposed on a surgical drape to indicate the presence of the surgical drape on the thermal treatment system and enable thermal treatment system operation as illustrated in FIG. 11. Specifically, drape 17 is substantially similar to the mechanical key drape described above except that an optical key 45 is preferably disposed on the non-sterile side of the drape. Optical key 45 may be attached to the drape via a band 14 or by any other fastening technique (e.g., string, chain, directly fastened or mounted on the drape via adhesives, etc.). Band 14 may be attached to the drape via any suitable adhesive, while the band may engage the optical key in any manner capable of securing the optical key to the drape. Optical key 45 is substantially rectangular wherein the proximal end of optical key 45 includes a substantially elliptical opening 3 having a major axis extending along the optical key shorter dimension. Opening 3 is of sufficient size to enable band 14 to traverse the opening and secure the optical key to the drape. However, the key and opening may be of any size or shape capable of securing the key to the drape and indicating drape presence to the thermal treatment system. Optical key 45 further includes an array of holes 46 defined in the distal portion of the optical key in a prearranged fashion. The pattern of holes 46 identifies optical key 45 and drape 17 to the thermal treatment system as described below. Drape 17 is placed over a thermal treatment system wherein a portion of the drape is pushed down into and conforms to the basin to form a drape receptacle as described above. Optical key 45 is inserted into a substantially rectangular key receptacle disposed within the thermal treatment system as described below wherein the optical key is oriented such that the optical key surfaces containing holes 46 are substantially horizontal. The key receptacle is disposed within a cabinet sidewall of the thermal treatment system to enable system operation wherein the key receptacle is oriented with its longer dimension substantially horizonal to accommodate the optical key. If desired, the key receptacle may be disposed in top surface 12. The optical key and key receptacle may be oriented in any fashion permitting identification of the drape by the thermal treatment system. In addition, the optical key may be disposed anywhere on the drape capable of enabling insertion of the optical key within the key receptacle, while holes 46 may be of any size or shape capable of identifying the drape as described below.

A thermal treatment system for utilizing optical key drape 17 is illustrated in FIGS. 12–13. Specifically, the thermal treatment system is substantially similar to the thermal treatment system described above for the mechanical key except that the thermal treatment system includes a key receptacle 4 and optical key reader 58. Receptacle 4 has dimensions slightly larger than the transverse cross-section of optical key 45 and is disposed and oriented within a cabinet sidewall as described above for receiving the optical key. Receptacle 4 extends into an optical key reader 58 disposed adjacent the key receptacle within the system cabinet interior. Reader 58 includes a plurality of light sources 49 and corresponding light detectors 50 that, in combination, sense the hole pattern defined in the optical key and generate corresponding signals for transmission to microprocessor 82. The microprocessor receives those signals and subsequently determines whether or not an appropriate key has been inserted into the reader. An additional light source and detector 56, 57, respectively, are disposed toward receptacle 4 and are utilized to sense the presence of optical key 45 within reader 58. Light detector 57 generates a corresponding signal for transmission to microprocessor 82 indicating whether or not an optical key is present within the reader.

Light sources 49, 56 are disposed on a lower ledge 47 that extends slightly below key receptacle 4 from a cabinet sidewall housing that key receptacle, while light detectors 50, 57 are respectfully disposed coincident light sources 49, 56 on an upper ledge 48 that extends slightly above key receptacle 4 from the cabinet sidewall housing the key receptacle. In other words, light sources 49, 56 and detectors 50, 57 are arranged on respective ledges 47, 48 such that detectors 50, 57 may each detect light from a corresponding light source 49, 56. A stop wall 54 is disposed between respective ledges 47, 48 at the ends of the ledges furthest from key receptacle 4 wherein stop wall 54 extends substantially parallel to the cabinet sidewall to permit the proper portion of optical key 45 to be inserted into reader 58. Stop wall 54 further aligns the hole pattern defined in the optical key with corresponding light sources and detectors 49, 50. A small ledge or track (not shown) may be disposed on stop wall 54 to support and maintain alignment of optical key 45 within reader 58. Light sources 49, 56 are powered by an appropriate power supply (not shown).

When optical key 45 is inserted into reader 58, each hole 46 is aligned between a corresponding light source 49 and detector 50. Light emitted from light sources 49 traverse holes 46 to corresponding detectors 50 wherein detectors 50 each generate a high level logic signal for transmission to microprocessor 82 in response to sensing light. Light source 56 is disposed toward key receptacle 4 such that light is projected from that light source onto the proximal portion of optical key 45 where no holes 46 are defined in order to detect the presence of the optical key within the reader. Since detector 57 does not detect light from light source 56 when optical key 45 is present in the reader (i.e., the optical key prevents detector 57 from detecting light from light source 56), that detector generates a low level logic signal for transmission to microprocessor 82 to indicate the presence of an optical key within the reader. The signals from detectors 50, 57 form a bit pattern that represents the presence of an optical key within reader 58 and the hole pattern of the optical key wherein the signal from each detector 50, 57 corresponds to a particular bit within the bit pattern. The signal from detector 57 preferably corresponds to the most significant bit of the bit pattern, however, the detector signals may be arranged in any fashion and may be associated with any bits in the bit pattern. The bit pattern formed by signals received from detectors 50, 57 is compared against a predetermined bit pattern in substantially the same manner described above for the mechanical key wherein each bit within the predetermined bit pattern represents the signal that is required to be received from a corresponding detector 50, 57 to enable system operation. The most significant bit of the predetermined bit pattern typically corresponds to detector 57 wherein this bit is preferably set to zero to require presence of the key within reader 58. Alternatively, the bits of the predetermined bit pattern may be arranged in any fashion capable of correspondence to detectors 50, 57 for verification of the key. When signals from detectors 50, 57 match corresponding bits of the predetermined bit pattern, the optical key is verified and system operation is enabled by microprocessor 82. The predetermined bit pattern may be configured to enable system operation for any combination of signals received from detectors 50, 57 and any quantity of detectors 50, 57 such that various optical keys having different hole patterns may be utilized with a particular thermal treatment system.

Operation of the thermal treatment system and optical key drape is described. Initially, drape 17 having optical key 45 is placed over a thermal treatment system to form a drape receptacle within a thermal treatment system basin as described above. Optical key 45 is inserted into key receptacle 4 and extends into reader 58 until abutting stop wall 54. Light from light sources 49, 56 are projected onto optical key 45 wherein the light emitted from light sources 49 traverse holes 46 within the optical key. Detectors 50 disposed coincident holes 46 detect the light from corresponding light sources 49 and generate high level logic signals for transmission to microprocessor 82 indicating the presence of a hole between that light source and detector. Detector 57 does not receive light from light source 56 since the emitted light is blocked by optical key 45, and generates a low level logic signal for transmission to microprocessor 82 indicating the presence of the key within the reader. Microprocessor 82 compares a bit pattern formed from the signals of detectors 50, 57 to a predetermined bit pattern indicating the signals required to be received from the detectors to verify the optical key and initiate system operation as described above. If the bit pattern formed from signals of detectors 50, 57 matches the predetermined bit pattern, microprocessor 82 enables power to temperature controller 16 to thermally treat basin 11. If the bit pattern formed from signals of detectors 50, 57 does not match the predetermined bit pattern, microprocessor 82 does not enable, or in other words, disables power to temperature controller 16 to cease or prevent thermal treatment of basin 11.

Detection of a drape on a thermal treatment system may further be accomplished via detection of certain bands or colors of light passed by a light filter patch disposed on the drape as illustrated in FIG. 14. Specifically, drape 17 is substantially similar to the bar code drape described above for FIG. 1 except that a light filter patch 72 is disposed on the drape to indicate the presence of the drape on the thermal treatment system. Light filter patch 72 may be disposed integral with the drape or within an opening defined in the drape and may include various materials (e.g., plastic, glass, drape material etc.) wherein the light filter patch is typically implemented by a conventional light filter that passes only certain bands or colors of light. Drape 17 is placed over the thermal treatment system wherein a portion of the drape is pushed down into and conforms to the basin to form a drape receptacle as described above, while light filter patch 72 is disposed coincident a light receiver embedded within the top surface of the thermal treatment system as described below. The light receiver directs light received from light filter patch 72 to light band filter circuitry disposed within the thermal treatment system. The light band filter circuitry includes a plurality of filters wherein the filters identify the bands of light received by the light receiver to determine the presence of the drape on the thermal treatment system and to enable thermal treatment system operation as described below. The light filter patch may be of any size and may be disposed anywhere on the drape capable of passing bands or colors of light to the light receiver.

A thermal treatment system for utilizing the light filter drape is illustrated in FIGS. 15–16. The system is substantially similar to the bar code thermal treatment system described above for FIG. 2 except that the system includes a light receiver 59 disposed within top surface 12 of the system cabinet and light band filter circuitry 71 disposed within the thermal treatment system cabinet interior to identify the bands of light received by light receiver 59. Light receiver 59 directs light received from light filter patch 72 to light band filter circuitry 71. Light band filter circuitry 71 includes a plurality of narrow band filters 60, 62 and combinational logic (e.g., NOR gate 61 sand AND gate 63) wherein the narrow band filters are disposed in parallel with each other with each filter generating a high level logic signal in response to detecting a particular band of light. Filters 60, 62 are pre-set in accordance with light filter patch 72 such that system operation commences only when particular bands of light are received that coincide with the light bands passed by the light filter patch. This occurs when a drape is placed on the thermal treatment system with light filter patch 72 disposed coincident light receiver 59. Filters 60 detect the presence of extraneous bands of light (i.e., bands other than those passed by light filter patch 72), while filters 62 detect the desired bands of light for system operation (i.e., bands passed by light filter patch 72). The logic level signals generated by filters 60 are each connected to individual inputs of a NOR gate 61. NOR gate 61 is typically a conventional NOR gate that generates a high level logic signal when each filter 60 generates a low level logic signal (i.e., a NOR gate generates a high level logic signal when all of its inputs are low) or, in other words, when no extraneous bands of light are received by light receiver 59. The individual logic level signals generated by filters 62 and the output of NOR gate 61 are each connected to individual inputs of an AND gate 63 to produce a signal that is sent to microprocessor 82 indicating whether or not system operation may commence. AND gate 63 is typically a conventional AND gate that generates a high level logic signal when the outputs generated from NOR gate 61 and filters 62 are each a high level logic signal (i.e., an AND gate generates a high level logic signal when all of its inputs are high) or, in other words, when the desired light bands are received by receiver 59 without other extraneous light bands, thereby indicating presence of the drape on the thermal treatment system. When microprocessor 82 receives a high level logic signal from AND gate 63 indicating the presence of drape 17 on the thermal treatment system, the microprocessor enables thermal treatment system operation. When the drape is not present on the thermal treatment system, extraneus bands of light are present within the light received by light receiver 59. Filters 60 produce high level logic signals in response to detecting these extraneous light bands, thereby causing NOR gate 61 to generate a low level logic signal (i.e., a NOR gate generates a low level logic signal when any of its inputs are high). The low level logic signal produced by NOR gate 61 causes AND gate 63 to generate a low level logic signal (i.e., an AND gate generates a low level logic signal when any of its inputs are low), thereby indicating the absence of drape 17 on the thermal treatment system. In addition, filters 62 may generate low level logic signals when desired bands of light are not detected within light received by light receiver 59, thereby causing AND gate 63 to generate a low level logic signal indicating absence of the drape on the thermal treatment system. In response to a low level logic signal from AND gate 63, microprocessor 82 does not enable or, in other words, disables thermal treatment system operation.

Operation of the thermal treatment system and light filter drape is described. Initially, drape 17 is placed over a thermal treatment system to form a drape receptacle within a thermal treatment system basin as described above with light filter patch 72 disposed coincident light receiver 59. Filters 60, 62 of light band filter circuitry 71 are each configured to detect a particular individual band or color of light. When drape 17 is placed over the thermal treatment system with light filter patch 72 disposed coincident light receiver 59, light traverses light filter patch 72 wherein the light filter patch passes only certain bands of light to light receiver 59. The bands passed by light filter patch 72 correspond to the bands detectable by filters 62 such that only those bands detected by filters 62 are passed by filter patch 72. Light receiver 59 receives the light bands from light filter patch 72 and distributes the light bands to narrow band filters 60, 62 of light band filter circuitry 71. Filters 60, 62 are configured to generate a high level logic signal in response to detecting a particular band of light. Since only light bands detectable by filters 62 are present when drape 17 is placed over the thermal treatment system, filters 62 detect these light bands and generate high level logic signals, while filters 60, configured to detect other light bands, do not detect these light bands and generate low level logic signals. The low level logic signals from filters 60 are connected to inputs of NOR gate 61 wherein the NOR gate produces a high level NOR gate output. The high level NOR gate output and the high level logic signals from filters 62 are connected to individual inputs of AND gate 63 wherein the AND gate generates a high level logic signal that informs microprocessor 82 of the drape presence on the thermal treatment system. Microprocessor 82 subsequently enables power to temperature controller 16 to thermally treat basin 11. When drape 17 is not disposed over the thermal treatment system, light receiver 59 receives extraneous bands of light. Filters 60, 62 generate high level logic signals in response to detecting their particular light bands. NOR gate 61 produces a low level logic signal, based on high level logic signals received from filters 60, that causes AND gate 63 to produce a low level logic signal (i.e., the low output from NOR gate 61 forces AND gate 63 to produce a low output). In addition, filters 62 may generate low level logic signals when desired bands of light are not detected within light received by light receiver 59, thereby causing AND gate 63 to produce a low level logic signal as described above. The low output from AND gate 63 is sent to microprocessor 82 to indicate the absence of the drape on the thermal treatment system wherein the microprocessor does not enable or, in other words, disables power to temperature controller 16 to cease or prevent thermal treatment of basin 11. The system and drape may include any quantity of light patches on the drape and corresponding light receivers and circuits disposed about the thermal treatment system to detect the presence of the drape on the system in substantially the same manner described above wherein the circuit outputs may be combined in any manner (e.g., AND, OR, etc.) to verify presence of the drape on the system.

Figure 17:
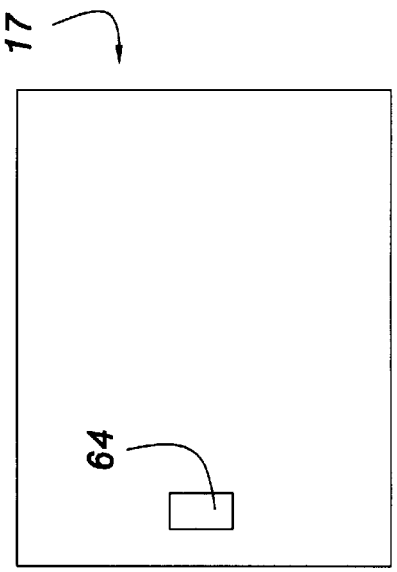
FIG. 17 is a top view in plan of a surgical drape having reflective material for reflecting light to indicate the presence of the drape on a thermal treatment system according to a further embodiment of the present invention.

An alternative embodiment that utilizes light to indicate the presence of a drape on thermal treatment system is illustrated in FIG. 17. Specifically, drape 17 is substantially similar to the bar code drape described above for FIG. 1 except that the drape may include reflective material segment 64 preferably disposed on the non-sterile side of the drape. Reflective material segment 64 may be disposed or affixed to the drape via any conventional adhesives or fastening techniques. Drape 17 is placed over the thermal treatment system wherein a portion of the drape is pushed down into and conforms to the basin to form a drape receptacle as described above, while reflective material segment 64 is disposed coincident a light source and detector arrangement embedded within the top surface of the thermal treatment system described below. Light emitted from the light source is reflected by reflective material segment 64 and sensed by the detector to indicate the presence of the drape on the thermal treatment system and to enable thermal treatment system operation as described below. Reflective material segment 64 may be of any size and may be disposed integral with or attached to the drape at any location capable of reflecting light from the light source toward the detector. Alternatively, the drape may be constructed of sufficiently reflective material capable of reflecting light with adequate intensity to indicate the presence of the drape on the thermal treatment system and to enable thermal treatment system operation in substantially the same manner described above.

Figure 18:
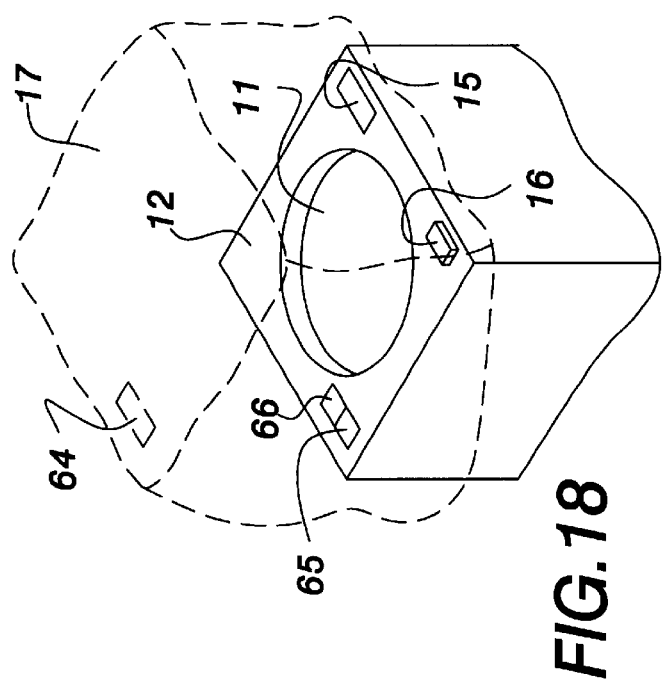
FIG. 18 is an exploded view in perspective of the surgical drape of FIG. 17 placed over a thermal treatment system having a light source for emitting light and a light detector for detecting the emitted light reflected from the drape to verify the presence of the drape on the thermal treatment system and to enable thermal treatment system operation.
Figure 19:
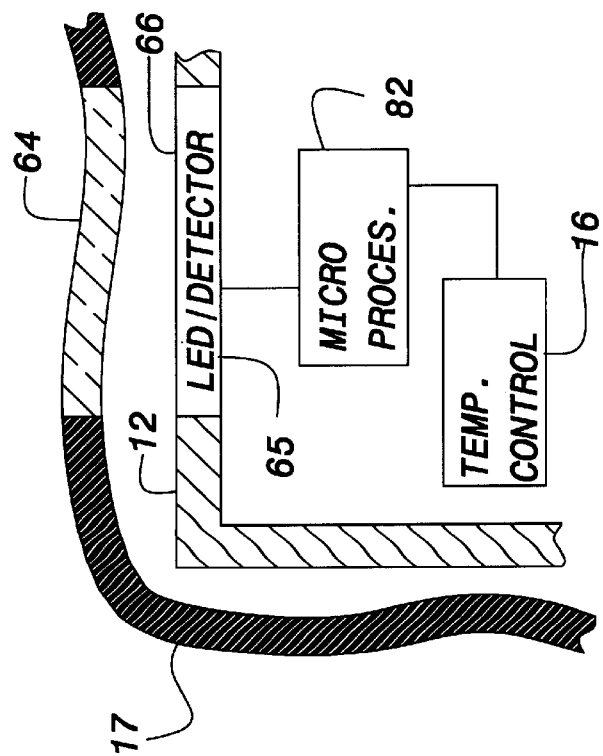
FIG. 19 is a side view in elevation and partial section of the thermal treatment system of FIG. 18 schematically illustrating the light source and light detector arrangement for detecting the presence of the drape on the thermal treatment system and enabling thermal treatment system operation.

A thermal treatment system for utilizing the reflective drape is illustrated in FIGS. 18–19. Specifically, the thermal treatment system is substantially similar to the bar code thermal treatment system described above for FIG. 2 except that the system includes a light source 65, preferably a light emitting diode (LED) that emits light of a particular light band or color, and a corresponding light detector 66 configured to detect the light emitted from the light source. Light source 65 and detector 66 are typically embedded adjacent each other within cabinet top surface 12, however, the light source and detector may be disposed anywhere on the thermal treatment system capable of detecting the presence of the drape. Light source 65 and detector 66 are typically implemented by conventional light sources or diodes and light detectors, respectively. Light source 65 emits light toward reflective material segment 64 wherein the emitted light is reflected back from the reflective material segment towards detector 66. Alternatively, the drape may be constructed of sufficiently reflective material wherein light from light source 65 is reflected back from the drape towards detector 66. Detector 66 generates a high level logic signal in response to detecting light having a band equivalent to the light emitted from the light source and an intensity exceeding a predetermined threshold. The threshold is utilized to prevent scattered light from the light source or ambient light within the surrounding environment form triggering the detector and enabling system operation as described below. The signal generated by detector 66 is transmitted to microprocessor 82 to indicate whether or not the drape is present on the thermal treatment system. When microprocessor 82 receives a high level logic signal indicating presence of the drape on the thermal treatment system, the microprocessor enables thermal treatment system operation.

In operation, initially, drape 17 is placed over a thermal treatment system to form a drape receptacle within a thermal treatment system basin as described above with reflective material segment 64 disposed coincident the light source and detector arrangement. Light source 65 emits light toward reflective material segment 64 wherein the emitted light is reflected from reflective material segment 64 back toward detector 66. Detector 66 receives the light reflected from reflective material segment 64 and generates a high level logic signal when the received light has a band equivalent to the light emitted from light source 65 and its intensity exceeds a predetermined threshold. Upon receiving the high level logic signal from detector 66 indicating presence of the drape on a thermal treatment system, microprocessor 82 enables power to temperature controller 16 to thermally treat basin 11. When drape 17 is not present on the thermal treatment system, light emitted from light source 65 is not reflected toward detector 66 wherein detector 66 only detects light existing within its surrounding environment and/or scattered from light source 65. The detected light is generally not of the desired band and is of insufficient intensity to exceed the predetermined threshold wherein detector 66 produces a low level logic signal for transmission to microprocessor 82. Microprocessor 82 receives the low level logic signal from detector 66 indicating absence of the drape from the thermal treatment system and does not enable or, in other words, disables power to temperature controller 16 to cease or prevent thermal treatment of basin 11. Alternatively, drape 17 may be made of sufficiently reflective material with the intensity threshold of detector 66 set accordingly to enable detection of the drape on the thermal treatment system in substantially the same manner described above. The system and drape may include any quantity of reflective material segments (e.g., at least one) disposed on the drape and any quantity of light sources and detectors (e.g., at least one) disposed about the system to detect the presence of the drape in substantially the same manner described above wherein the detector outputs may be combined in any manner (e.g., AND, OR, etc.) to verify the presence of the drape on the system.

Figure 20:
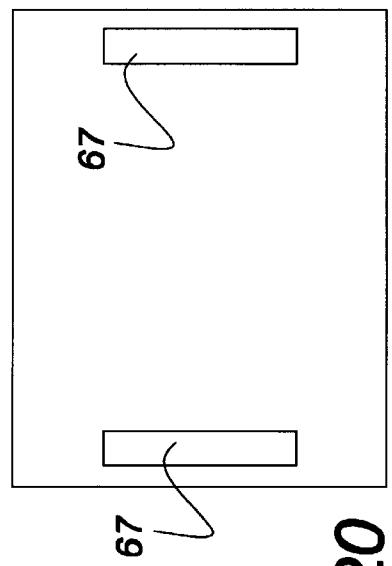
FIG. 20 is a top view in plan of a surgical drape having magnetic media to indicate the presence of the drape on a thermal treatment system according to yet another embodiment of the present invention.

The presence of a drape on a thermal treatment system may also be detected by utilizing a drape including magnetic media as illustrated in FIG. 20. Specifically, drape 17 is substantially similar to the bar code drape described above for FIG. 1 except that the drape includes magnetic media 67, preferably magnetic strips, disposed within the drape or on the sterile or non-sterile surface of the drape. Magnetic media 67 may be any conventional magnetic media formed into any quantity of strips or other shapes (e.g., at least one) and disposed on the drape in any fashion that enables detection of the media. By way of example only, drape 17 includes two magnetic strips 67 disposed toward opposite sides of the drape. Drape 17 is placed over the thermal treatment system wherein a portion of the drape is pushed down into and conforms to the basin to form a drape receptacle as described above, while magnetic media 67 are disposed coincident magnetic detectors embedded within the top surface of the thermal treatment system as described below. Alternatively, drape 17 may be constructed of a material including a magnetic pigment or resin additive that is detectable by the magnetic detectors when the drape is disposed over the thermal treatment system as described above. The magnetic detectors sense magnetic media 67 or the magnetic pigment or resin additive to indicate the presence of the drape on the thermal treatment system and to enable thermal treatment system operation as described below. The magnetic media and/or pigment or resin additive may further be utilized to maintain the drape position on the thermal treatment system since the magnetic media and/or pigment or resin additive may be attracted to metallic objects, such as objects disposed on the system top surface, the system top surface itself and/or the magnetic detectors, to secure the drape on the thermal treatment system.

Figure 21:
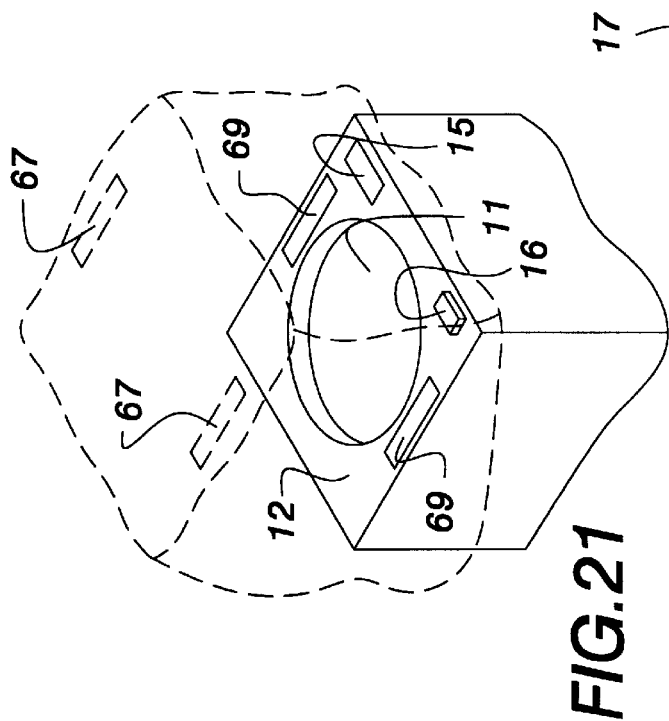
FIG. 21 is an exploded view in perspective of the surgical drape of FIG. 20 placed over a thermal treatment system having magnetic detectors for sensing the drape magnetic media to verify the presence of the drape on the thermal treatment system and to enable thermal treatment system operation.
Figure 22:
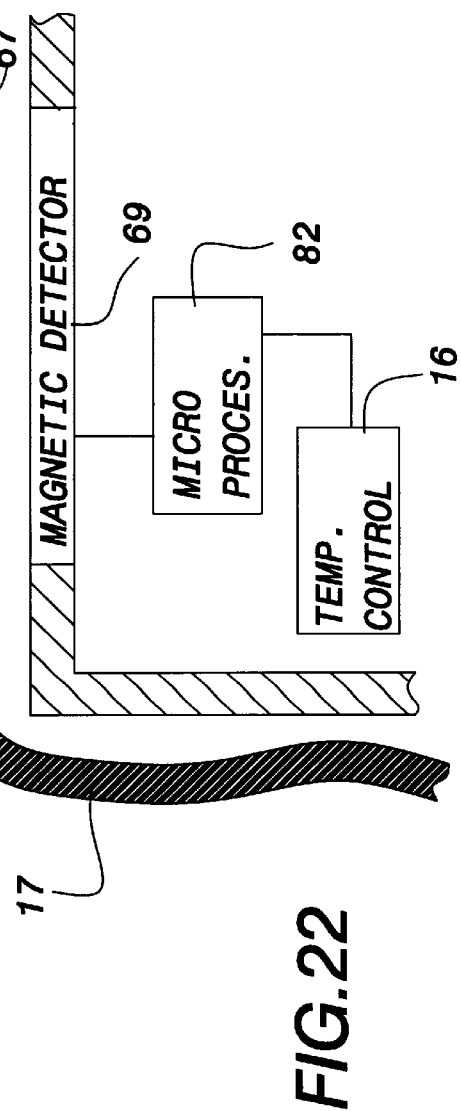
FIG. 22 is a side view in elevation and partial section of the thermal treatment system of FIG. 21 schematically illustrating a thermal treatment system magnetic detector for detecting the presence of the drape on the thermal treatment system and enabling thermal treatment system operation.

A thermal treatment system suitable for the use with the magnetic drape is illustrated in FIGS. 21–22. Specifically, the thermal treatment system is substantially similar to the bar code thermal treatment system described above for FIG. 2 except that the system includes magnetic detectors 69 disposed within top surface 12 of the system cabinet. Detectors 69 are each conventional magnetic detectors that generate a high level logic signal upon detecting magnetic media. The drape and thermal treatment system may include any quantity of magnetic media disposed within or on the drape and any quantity of associated detectors disposed within the thermal treatment system wherein the detectors may be disposed within the thermal treatment system in any manner capable of detecting the presence of the drape. By way of example only, the thermal treatment system includes two magnetic detectors with each detector associated with a magnetic strip disposed on drape 17. Microprocessor 82 receives a signal from each detector 69 indicating whether or not the detector has sensed its corresponding magnetic media 67 or the magnetic pigment or resin additive. In other words, the signals from each detector 69 indicates whether or not that detector has sensed the presence of the drape on the thermal treatment system. In response to receiving a high level logic signal from each detector 69 indicating the presence of the drape on the thermal treatment system, the microprocessor enables thermal treatment system operation. When microprocessor 82 receives a low level logic signal from any of the detectors 69 indicating absence of the drape from the thermal treatment system, the microprocessor does not enable or, in other words, disables thermal treatment system operation. It is to be understood that the output of magnetic detectors 69 may be combined in any manner (e.g., AND, OR, etc.) to determine the presence of the drape on the thermal treatment system and enable system operation (e.g., any percentage of the detectors may be required to detect the drape to enable system operation).

Operation of the thermal treatment system with a magnetic drape is described. Initially, drape 17 having magnetic media 67 is disposed over a thermal treatment system to form a drape receptacle within a thermal treatment system basin as described above with magnetic media 67 respectively disposed coincident corresponding magnetic detectors 69. Alternatively, drape 17 may be constructed of material including a magnetic pigment or resin additive detectable by magnetic detectors 69 wherein the drape is disposed over the thermal treatment system to form a drape receptacle within the thermal treatment system basin as described above. Detectors 69 detect the presence of magnetic media 67 or the magnetic pigment or resin additive, and each detector generates a high level logic signal for transmission to microprocessor 82. Microprocessor 82 receives a high level logic signal from each detector 69 indicating presence of the drape on a thermal treatment system and enables power to temperature controller 16 to thermally treat basin 11. When drape 17 is absent from the thermal treatment system, detectors 69 do not detect magnetic media 67 or the magnetic pigment or resin additive, and each detector generates a low level logic signal for transmission to microprocessor 82. Microprocessor 82, in response to receiving a low level logic signal from any detector 69 indicating the absence of the drape from the thermal treatment system, does not enable or, in other words, disables power to temperature controller 16 to cease or prevent thermal treatment of basin 11.

It will be appreciated that the embodiments described above and illustrated in the drawings represent only a few of the many ways of implementing a method and apparatus of the present invention for ensuring sterility of surgical drapes used with surgical equipment.

The microprocessor of the embodiments of the present invention may be implemented by any memory or storage devices in conjunction with general circuitry or combinational logic to perform the processing and enable power to the temperature controllers. Memory equivalents include conventional semi-conductor memories, optical memories, or any other storage devices capable of storing information. Further, the microprocessor of the bar code embodiment may be configured to utilize the bar code to maintain or index any information relating to a particular drape or plurality of drapes.

The thermal treatment systems of the present invention are capable of including sound or visual indicators notifying when a drape is in a non-sterile condition or absent from thermal treatment system. Such indicators include an alarm, buzzer, colored light, speech synthesizer or any other indicator used for specifying a condition or state of an object.

The memory conservation by deletion of old data within the bar code embodiment may be alternatively accomplished by use of a queue. Entries are added to the queue until the queue becomes full. After the queue becomes full, the oldest entries are removed as new entries are added. The queue may be implemented by software, or may be realized in hardware.

The mechanical drape keys may include any quantity of indentations (i.e., including zero or no indentations) defined on any edge of the key to form an identification pattern for a drape. The mechanical key may be inserted into the receptacle at any orientation wherein the receptacle and tumbler may be disposed anywhere on the system capable of receiving the key and may be oriented in any fashion capable of verifying the mechanical key, and the tumbler may include any number of plungers or other devices for sensing the indentations. Further, the predetermined bit pattern may be set to any pattern corresponding to a key wherein not all plungers need to have their associated contacts interface to validate a key. This permits several variations of key indentations to be utilized on a thermal treatment system. Similarly, the optical key may be inserted into the receptacle at any orientation and may utilize various quantities of holes (i.e., including zero or no holes) and/or hole patterns wherein the receptacle and reader may be disposed anywhere on the system capable of receiving the keys may be oriented in any fashion capable of verifying the optical key, and the reader may include any quantity of conventional or other light sources and detectors (e.g., at least one) that may respectively emit and detect any bands or colors of light for verifying the key. The predetermined bit pattern may be any pattern wherein not all detectors need to detect light to validate the key. This permits several variations of hole patterns to be utilized on a thermal treatment system. The mechanical and optical keys may be attached anywhere to the drape, via any fastening technique, such that the mechanical and optical keys are capable of being inserted into the respective key receptacles when the drape is placed over the thermal treatment system. In addition, the signals from the plungers and light detectors from the respective key embodiments may be examined individually or in any combination by the microprocessor to determine drape presence and enable thermal treatment system operation.

The light band filters may be configured to detect any bands or colors of light wherein the drape light filter patch passes any quantity of specified bands (e.g., at least one). There may be any quantity of light filter patches disposed anywhere on the drape wherein any quantity of bands may be detected to enable operation of the system. Further, the drape may include any quantity of filter patches (e.g., at least one), while the thermal treatment system may include any quantity of light receivers and light band filter circuits (e.g., at least one receiver and circuit) disposed anywhere on the system capable of verifying the light bands wherein the circuitry output may be combined in various manners (e.g., AND, OR etc.) to determine the presence of the drape. The drape light filter patch and light band filters may be implemented by conventional patches and filters or other devices capable of filtering and identifying light. The light band filter circuitry may include any quantity of light band filters (e.g., at least one) and may be implemented by any circuitry or other device capable of identifying the bands.

It is to be understood that the light filter patch described above may also be implemented by conventional filters or other mechanisms (e.g., a lens or colored or dark material) that pass light at an altered (e.g., increased or decreased) intensity, or prevent passage of light. Drape detection is accomplished in substantially the same manner described above except that the light receiver generates a signal for transmission to the microprocessor indicating the presence of the drape on the thermal treatment system without the use of associated light band filter circuitry. The light receiver may be implemented by a conventional light detector or other device that measures and compares intensity of received light to an intensity threshold, or merely detects the presence of light to generate a corresponding signal for transmission to the microprocessor. In particular, when a light filter patch is utilized that alters light intensity, the light receiver measures and compares intensity of received light to a predetermined light intensity threshold. In response to the comparison, the light receiver generates a signal for transmission to the microprocessor indicating presence of the drape on the thermal treatment system to control thermal treatment system operation. The intensity threshold may be configured accordingly such that the received light intensity may exceed or be less than the threshold, depending upon the particular application and/or light filter patch utilized, to enable thermal treatment system operation. When a light filter patch is utilized that prevents passage of light, the light receiver detects the absence of light and generates a signal for transmission to the microprocessor indicating presence of the drape on the thermal treatment system to control thermal treatment system operation. The drape may include any quantity of the various light filter patches described above (e.g., at least one), while the thermal treatment system may include any quantity of corresponding light receivers (e.g., at least one) and associated light band filter circuitry, if necessary, with outputs of the receivers and/or circuits combined as described above.

The reflective material segment may be disposed on the drape in any quantity (e.g., at least one) and may be any shiny material capable of reflecting light toward the detector. Further, the drape may be constructed of sufficiently reflective material to reflect light. The light source and detectors may be disposed anywhere about the thermal treatment system in any quantity (e.g., at least one) and configured to emit and receive any bands or colors of light. Further, the light detector thresholds may be set to any threshold for different applications having various intensities of reflected light. The light sources and detectors may be implemented by conventional sources and detectors or any other devices capable of emitting and detecting light.

The drape may include any magnetic media detectable by a magnetic detector, or the drape may be constructed of material including any magnetic pigment or resin additive capable of detection by a magnetic detector. Further, there may be any quantity of magnetic media (e.g., at least one) disposed on the drape and any quantity of detectors (e.g., at least one) disposed about the thermal treatment system wherein the detectors are typically implemented by conventional magnetic detectors or any other devices capable of detecting the magnetic media or magnetic pigment. The outputs of the magnetic detectors may be combined in various manners (e.g., AND, OR, etc.) to detect the presence of the drape on the thermal treatment system.

Although the preferred embodiments disclose several techniques of detecting the presence of the drape, the present invention is not limited to those embodiments. Any number of identification codes or tags and associated devices for reading such codes or tags may be implemented according to the present invention. Such schemes may include any optically sensed codes or tags whether or not they are visible to a user, such as character recognition, magnetic codes or tags, voice recognition devices, and any other manners of uniquely tagging and identifying objects.

From the foregoing description it will be appreciated that the invention makes available a novel method and apparatus for ensuring sterility of surgical drapes used with surgical equipment wherein a thermal treatment system including a drape for containing sterile liquid detects the drape's presence on the system via a detector disposed within the thermal treatment system that senses indicia or other objects disposed on the drape. In addition, the invention prevents operation of the system if a non-sterile drape or no drape is disposed on the system.

Having described preferred embodiments of a new and improved method and apparatus for ensuring sterility of surgical drapes for use with surgical equipment, it is believed that other modifications, variations and changes will be suggested to those skilled in the art in view of the teachings set forth herein. It is therefore to be understood that all such variations, modifications and changes are believed to fall within the scope of the present invention.

What is claimed is:

1. An apparatus for ensuring sterility of a sterile medium contained within a thermal treatment system basin by detecting the presence of a sterile drape providing a sterile field above the basin for thermal treatment of the sterile medium, said apparatus comprising:

a thermal treatment system for thermally treating the sterile medium, said thermal treatment system including at least one basin;

a surgical drape covering and substantially conforming to said at least one basin to serve as a drape container for the sterile medium, said surgical drape including a surgical drape identifier for indicating the presence of said surgical drape on said thermal treatment system;

a detector to sense said surgical drape identifier and to determine the presence of said surgical drape on said thermal treatment system; and a controller to enable said thermal treatment system to thermally treat the sterile medium in response to said detector indicating the presence of said surgical drape on said thermal treatment system.

2. The apparatus of claim 1 wherein said surgical drape identifier includes a tag containing a bar code, and said detector includes:

a bar code reader;

a memory to store bar codes read by said bar code reader wherein the bar codes identify non-sterile previously used drapes; and a processor to determine the presence of a sterile surgical drape on said thermal treatment system by comparing the bar code of said surgical drape to bar codes stored in said memory;

wherein said controller enables said thermal treatment system in response to said processor determining that the bar code of said surgical drape does not match any of the bar codes identifying non-sterile previously used drapes stored in said memory.

3. The apparatus of claim 2 wherein said memory further includes information associated with surgical drapes that is stored based on drape bar codes, and said processor includes a drape manager to perform drape management tasks that utilize said information.

4. The apparatus of claim 1 wherein said surgical drape identifier includes a mechanical key.

5. The apparatus of claim 4 wherein said mechanical key includes an identification code defined by at least one indentation formed in said key, and said detector includes:

a tumbler to ascertain the identification code; and a processor to verify the identification code against a predetermined code indicating valid keys to determine the presence of said surgical drape on said thermal treatment system.

6. The apparatus of claim 1 wherein said surgical drape identifier includes an optical key.

7. The apparatus of claim 6 wherein said optical key includes an identification code defined by at least one hole formed in said key in a particular pattern, and said detector includes:

an optical key reader to ascertain the particular pattern and identification code; and a processor to verify the identification code against a predetermined code indicating valid keys in order to determine the presence of said surgical drape on said thermal treatment system.

8. The apparatus of claim 1 wherein said surgical drape identifier includes at least one light filter patch.

9. The apparatus of claim 8 wherein each said light filter patch passes at least one specific band of light, and said detector includes:

at least one light receiver to receive light from a corresponding light filter patch; and at least one light band filter circuit for receiving light from a corresponding light receiver and verifying that the light received from said corresponding light receiver contains only each specific band of light passed by said corresponding light filter patch to determine the presence of said surgical drape on said thermal treatment system.

10. The apparatus of claim 8 wherein each said light filter patch passes light at an altered intensity, and said detector includes:

at least one light receiver to receive and measure intensity of light passed by a corresponding light filter patch and to compare the intensity of the received light to a predetermined light intensity threshold to determine the presence of said surgical drape on said thermal treatment system.

11. The apparatus of claim 8 wherein each said light filter patch prevents passage of light, and said detector includes:

at least one light receiver to detect the absence of light from a corresponding light filter patch to determine the presence of said surgical drape on said thermal treatment system.

12. The apparatus of claim 1 wherein said surgical drape identifier includes at least one reflective material segment.

13. The apparatus of claim 12 wherein said detector includes:

at least one light source for emitting a particular band of light; and at least one light detector for detecting said particular band of light emitted from a corresponding light source and reflected by a corresponding reflective material segment to determine the presence of said surgical drape on said thermal treatment system.

14. The apparatus of claim 1 wherein said surgical drape identifier includes reflective material used for construction of said surgical drape.

15. The apparatus of claim 14 wherein said detector includes:

at least one light source for emitting a particular band of light; and at least one light detector for detecting said particular band of light emitted from a corresponding light source and reflected by said drape to determine the presence of said surgical drape on said thermal treatment system.

16. The apparatus of claim 1 wherein said surgical drape identifier includes at least one magnetic medium.

17. The apparatus of claim 16 wherein said detector includes at least one magnetic detector for sensing a corresponding magnetic medium to determine the presence of said surgical drape on said thermal treatment system.

18. The apparatus of claim 1 wherein said surgical drape identifier includes a magnetic pigment or resin additive incorporated into material used for construction of said surgical drape.

19. The apparatus of claim 18 wherein said detector includes at least one magnetic detector for sensing said magnetic pigment or resin additive to determine the presence of said surgical drape on said thermal treatment system.

20. A device for use in a surgical apparatus to ensure sterility of liquid being temperature controlled, wherein said surgical apparatus includes at least one temperature controlled basin and a detector fixedly positioned relative to said surgical apparatus, and said device comprises a drape containing a drape identifier adapted and disposed to be sensed by said detector to determine the presence of said drape on said surgical apparatus when said drape is placed on said surgical apparatus with said drape identifier positioned to be detectable by said detector and a portion of said drape is disposed in said at least one basin to form a drape container in the basin for containing and maintaining said liquid, wherein said drape identifier indicates the presence of said drape on said surgical apparatus, and said surgical apparatus includes a controller for enabling operation of said surgical apparatus in response to determining the presence of said drape on said surgical apparatus thereby preventing operation of said surgical apparatus without a drape container.

21. The device of claim 20 wherein said drape identifier includes a tag containing a bar code.

22. The device of claim 20 wherein said drape identifier includes a mechanical key.

23. The device of claim 20 wherein said drape identifier includes an optical key.

24. The device of claim 20 wherein said drape identifier includes at least one light filter patch.

25. The device of claim 20 wherein said drape identifier includes at least one reflective material segment.

26. The device of claim 20 wherein said drape identifier includes reflective material used for construction of said drape.

27. The device of claim 20 wherein said drape identifier includes at least one magnetic medium.

28. The device of claim 20 wherein said drape identifier includes a magnetic pigment or resin additive incorporated into material used for construction of said drape.

29. A method for ensuring sterility of a sterile medium contained within at least one thermal treatment system basin by detecting the presence of a sterile surgical drape disposed over a thermal treatment system wherein the sterile surgical drape provides a sterile field above the basin, said method comprising the steps of:
  (a) physically placing a drape identifier on surgical drapes;
  (b) determining the presence of a drape placed on the thermal treatment system by detecting in the thermal treatment system said drape identifier of said drape placed on the thermal treatment system; and
  (c) enabling temperature control of each basin only in response to detection of said drape identifier.

30. The method of claim 29 wherein said drape identifier includes a tag containing a bar code, and step (b) further includes:
  (b.1) detecting said bar code to determine the presence and sterility of said drape placed on the thermal treatment system; and step (c) further includes:
  (c.1) storing bar codes of previously used drapes in a memory wherein the bar codes identify non-sterile previously used drapes;
  (c.2) determining the presence and sterility of said drape placed on the thermal treatment system by comparing the bar code of that drape to bar codes stored in said memory; and
  (c.3) enabling said temperature control in response to determining that the bar code of said drape does not match any of the bar codes identifying non-sterile previously used drapes stored in said memory.

31. The method of claim 30 wherein step (c) further includes:
  (c.4) storing information associated with surgical drapes in said memory based on the drape bar codes; and
  (c.5) performing drape management tasks utilizing said stored information associated with surgical drapes.

32. The method of claim 29 wherein said drape identifier includes a mechanical key, and step (b) further includes:
  (b.1) detecting and verifying in the thermal treatment system, via a tumbler, said mechanical key to determine the presence of said drape on the thermal treatment system.

33. The method of claim 29 wherein said drape identifier includes an optical key, and step (b) further includes:
  (b.1) detecting and verifying in the thermal treatment system, via an optical key reader, said optical key to determine the presence of said drape on the thermal treatment system.

34. The method of claim 29 wherein said drape identifier includes at least one light filter patch that passes at least one specific band of light, and step (b) further includes:
  (b.1) verifying in the thermal treatment system, via at least one light receiver and associated light band filter circuit, that light received by a corresponding light receiver contains only each said specific band of light passed by a corresponding light filter patch to determine the presence of said drape on the thermal treatment system.

35. The method of claim 29 wherein said drape identifier includes at least one light filter patch that passes light at an altered intensity, and step (b) further includes:
  (b.1) receiving in the thermal treatment system, via at least one light receiver, light passed by a corresponding light filter patch;
  (b.2) measuring, via said at least one light receiver, intensity of the received light; and
  (b.3) comparing the intensity of the received light, via said at least one light receiver, to a predetermined intensity threshold to determine the presence of said surgical drape on the thermal treatment system.

36. The method of claim 29 wherein said drape identifier includes at least one light filter patch that prevents passage of light, and step (b) further includes:
  (b.1) detecting in the thermal treatment system, via at least one light receiver, the absence of light from a corresponding light filter patch to determine the presence of said surgical drape on the thermal treatment system.

37. The method of claim 29 wherein said drape identifier includes at least one reflective material segment, wherein the thermal treatment system includes at least one light source for emitting a specific band of light and a corresponding light detector for detecting the specific band of light, and step (b) further includes:

(b.1) detecting in the thermal treatment system, via each said light detector, light emitted from a corresponding light source and reflected by a corresponding reflective material segment to determine the presence of said drape on the thermal treatment system.

38. The method of claim 29 wherein said drape identifier includes reflective material used for construction of said drape, wherein the thermal treatment system includes at least one light source for emitting a specific band of light and a corresponding light detector for detecting the specific band of light, and step (b) further includes:

(b.1) detecting in the thermal treatment system, via each said light detector, light emitted from a corresponding light source and reflected by said drape to determine the presence of said drape on the thermal treatment system.

39. The method of claim 29 wherein said drape identifier includes at least one magnetic medium, and step (b) further includes:

(b.1) detecting in the thermal treatment system, via at least one magnetic detector, a corresponding magnetic medium to determine the presence of said drape on the thermal treatment system.

40. The method of claim 29 wherein said drape identifier includes a magnetic pigment or resin additive incorporated into material used for construction of said drape, and step (b) further includes:

(b.1) detecting in the thermal treatment system, via at least one magnetic detector, said magnetic pigment or resin additive to determine the presence of said drape on the thermal treatment system.

* * * * *